United States Patent
Tanaka et al.

(10) Patent No.: US 8,282,600 B2
(45) Date of Patent: Oct. 9, 2012

(54) BODY-INSERTABLE DEVICE AND LIQUID MEDICINE INJECTION METHOD

(75) Inventors: Shinsuke Tanaka, Hachioji (JP);
Hironobu Takizawa, Hachioji (JP);
Hironao Kawano, Hino (JP)

(73) Assignee: Olympus Corporation, Tokyo (JP)

( * ) Notice: Subject to any disclaimer, the term of this patent is extended or adjusted under 35 U.S.C. 154(b) by 1153 days.

(21) Appl. No.: 12/139,119

(22) Filed: Jun. 13, 2008

(65) Prior Publication Data
US 2008/0294143 A1    Nov. 27, 2008

Related U.S. Application Data

(63) Continuation of application No. PCT/JP2006/324974, filed on Dec. 14, 2006.

(30) Foreign Application Priority Data

Dec. 15, 2005 (JP) ................... 2005-362272

(51) Int. Cl.
*A61M 5/46* (2006.01)

(52) U.S. Cl. .......... 604/117; 604/506; 604/890.1; 604/891.1

(58) Field of Classification Search .......... None
See application file for complete search history.

(56) References Cited

U.S. PATENT DOCUMENTS

| 4,645,491 A | * | 2/1987 | Evans ............ 604/158 |
| 5,409,457 A | * | 4/1995 | del Cerro et al. ............ 604/521 |
| 2003/0085994 A1 | | 5/2003 | Fujita et al. |
| 2005/0124875 A1 | | 6/2005 | Kawano et al. |
| 2005/0246783 A1 | | 11/2005 | Christmann |

FOREIGN PATENT DOCUMENTS

| JP | 57-39776 | 8/1982 |
| JP | 5-245101 | 9/1993 |
| JP | 2003-325438 | 11/2003 |
| JP | 2005-288184 | 10/2005 |
| WO | WO 2005/065337 A2 | 7/2005 |

OTHER PUBLICATIONS

Extended Supplementary Partial European Search Report dated Dec. 2, 2010.

* cited by examiner

*Primary Examiner* — Long V. Le
*Assistant Examiner* — Farshad Negarestan
(74) *Attorney, Agent, or Firm* — Scully, Scott, Murphy & Presser, P.C.

(57) ABSTRACT

A body-insertable device is introduced into a desired part in a body for injecting a liquid medicine stored in a casing into the desired part. The body-insertable device includes a projecting portion which projects an injection needle injecting the liquid medicine toward the desired part; a detecting unit which detects a position relation between a biological tissue surface in the desired part and the injection needle; and a control unit. The control unit controls an amount of projection of the injection needle according to the position relation detected by the detecting unit, and controls a puncture depth of the injection needle from the biological tissue surface.

6 Claims, 30 Drawing Sheets

INJECTION NEEDLE 4

BODY-INSERTABLE DEVICE AND LIQUID MEDICINE INJECTION METHOD

CROSS-REFERENCE TO RELATED APPLICATIONS

This application is a continuation of PCT international application Ser. No. PCT/JP2006/324974 filed Dec. 14, 2006 which designates the United States, incorporated herein by reference, and which claims the benefit of priority from Japanese Patent Application No. 2005-362272, filed Dec. 15, 2005, incorporated herein by reference.

BACKGROUND OF THE INVENTION

1. Field of the Invention

The present invention relates to a body-insertable device having a local injection function which is introduced into a body and injects a liquid medicine into a desired part in the body and a liquid medicine injection method.

2. Description of the Related Art

A body-insertable device which extracts body fluid in a patient has been proposed. The body-insertable device has, in a capsule-type casing, a storage chamber which stores body fluid extracted from the inside of the body, and an input controlling mechanism which controls an input of the body fluid to the storage chamber. Upon reaching a desired part in the body such as a patient, the body-insertable device extracts the body fluid by predetermined control of the input controlling mechanism, and then stores the extracted body fluid in the storage chamber.

As a specific example of such a body-insertable device of the related art, there has been proposed a body-insertable device which has an extracting needle having, at its tip, an extracting portion having water absorbing properties, a driving mechanism which projects and houses the extracting needle from and in a casing, and a projection/housing controlling mechanism which controls the projecting operation and the housing operation of the extracting needle by the driving mechanism by an electromagnetic force (see Japanese Published Examined Application No. 57-39776). According to control of the projection/housing controlling mechanism, the driving mechanism of the body-insertable device projects the extracting needle from the casing, allows body fluid to adhere to the extracting portion at the tip of the extracting needle, and houses the extracting needle in the casing together with the extracting portion to which the body fluid adheres. In this manner, the body-insertable device extracts body fluid in the desired part in the body.

There has been also proposed a body-insertable device which directly supplies a liquid medicine to an affected part in the body by application of the above mechanism. The body-insertable device has an injection needle in place of the extracting needle of the body-insertable device described in Japanese Published Examined Application No. 57-39776, projects the injection needle from a casing, and then discharges the liquid medicine via the injection needle. In such a body-insertable device, the injection needle projected from the casing punctures the affected part in the body, and then injects the liquid medicine into the affected part.

SUMMARY OF THE INVENTION

A body-insertable device according to an aspect of the present invention is introduced into a desired part in a body for injecting a liquid medicine stored in a casing into the desired part. The body-insertable device includes a projecting portion which projects an injection needle injecting the liquid medicine toward the desired part, the injection needle having a plurality of angle detection markers each having a predetermined width in a longitudinal direction of the injection needle; an imaging unit which images an image including the injection needle projected from the casing; an angle detecting unit which detects the angle detection markers from the image, and calculates a puncture angle of the injection needle based on a result of the detection; and a control unit which controls a puncture depth of the injection needle from a biological tissue surface in the desired part based on the calculated puncture angle of the injection needle.

A body-insertable device according to another aspect of the present invention includes a projecting portion which projects an injection needle injecting the liquid medicine toward the desired part; a discharging unit which discharges, from a tip of the injection needle, the liquid medicine colored in a color different from a biological tissue surface in the desired part; an imaging unit which images an image including the liquid medicine discharged onto the biological tissue surface via the injection needle; and a control unit performs an image processing for detecting spread of the liquid medicine on the biological tissue surface based on the image and controls a puncture depth of the injection needle from the biological tissue surface, according to a result of the image processing.

A body-insertable device according to still another aspect of the present invention includes a projecting portion which projects an injection needle injecting the liquid medicine toward the desired part; a detecting unit which detects a position relation between a biological tissue surface in the desired part and the injection needle; and a control unit which controls an amount of projection of the injection needle according to the position relation detected by the detecting unit and controls a puncture depth of the injection needle from the biological tissue surface. The detecting unit includes a base frame which is connected in parallel with the injection needle reciprocated by driving of the projecting portion; a driving unit which rotatably drives the base frame about a rotating shaft formed at one end of the base frame; and a pressing unit which is rotatably provided at the other end of the base frame, rotatably drives the base frame, and presses the biological tissue surface The pressing unit of the base frame presses the biological tissue surface and initially arranges the injection needle in a predetermined position of the biological tissue surface. The control unit controls the puncture depth of the injection needle according to the position relation between the initially arranged injection needle and the biological tissue surface.

A liquid medicine injection method according to still another aspect of the present invention includes introducing a body-insertable device having a liquid medicine and an injection needle injecting the liquid medicine in a casing into a desired part in a body; projecting the injection needle from the body-insertable device to the desired part; detecting a position relation between a biological tissue surface in the desired part and the injection needle; and controlling the puncture depth of the injection needle from the biological tissue surface according to the detected position relation.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Preferred embodiments of a body-insertable device and a liquid medicine injection method according to the present invention will be described below in detail with reference to the drawings. The present invention is not limited to the embodiments.

Figure 1:
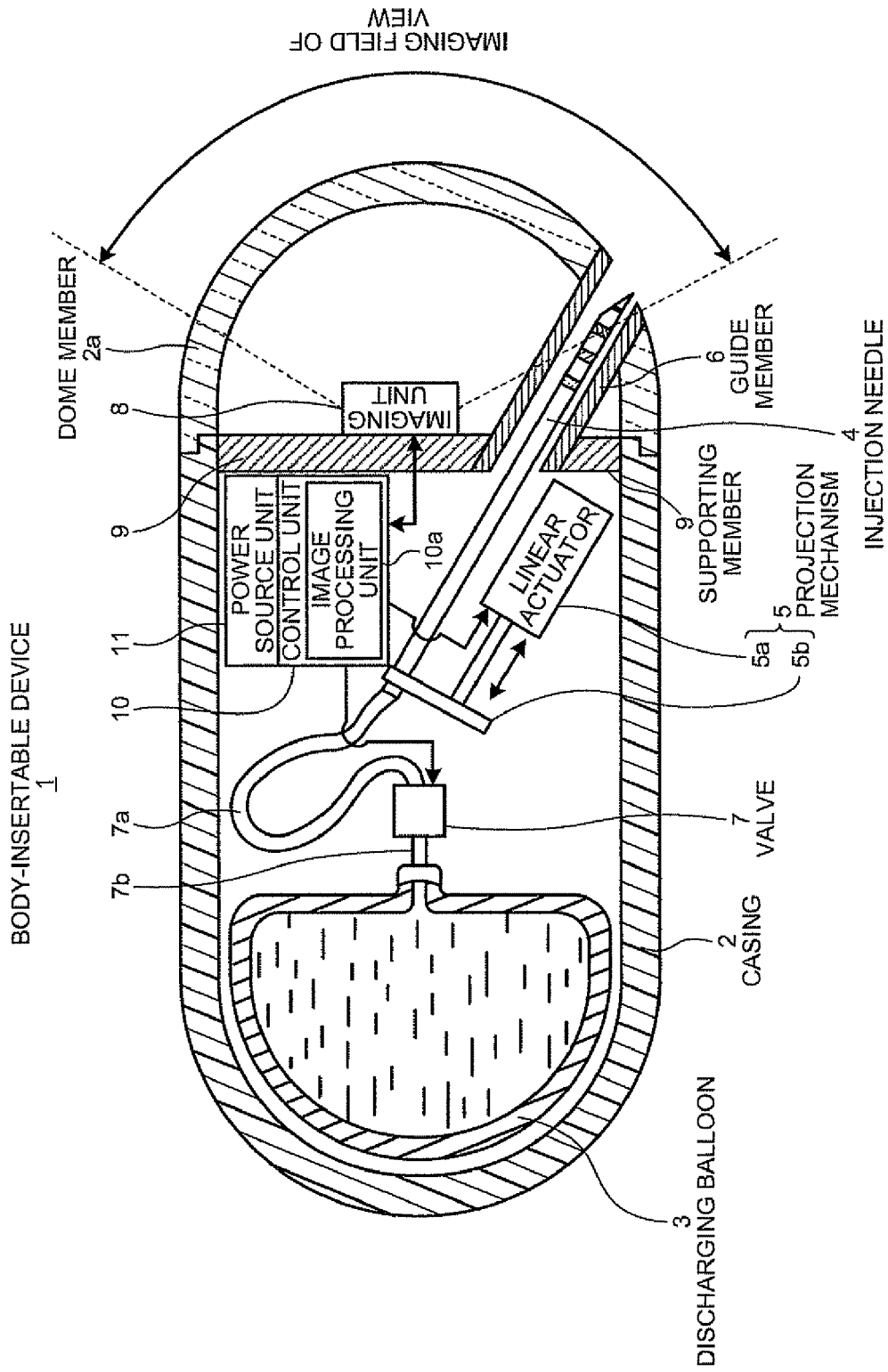
FIG. 1 is a sectional schematic diagram schematically illustrating a configuring example of a body-insertable device according to the first embodiment of the present invention.

FIG. 1 is a sectional schematic diagram schematically illustrating a configuring example of a body-insertable device according to a first embodiment of the present invention. A body-insertable device 1 has a local injection function, which is introduced into a body and injects a liquid medicine into a desired part in the body. Specifically, as illustrated in FIG. 1, the body-insertable device 1 has, in a casing 2, a discharging balloon 3 which forms a storage chamber storing the liquid medicine and discharges the liquid medicine, an injection needle 4 which injects the liquid medicine discharged by the discharging balloon 3 into the desired part in the body, a projection mechanism 5 which projects the injection needle 4 from the casing 2, and a guide member 6 which forms a projection opening of the injection needle 4. The body-insertable device 1 also has a valve 7 which is open- and close-driven to start or stop the discharging operation of the liquid medicine by the discharging balloon 3, a tube 7a which forms a circulation duct line of the liquid medicine circulating between the injection needle 4 and the valve 7, and a tube 7b which forms a circulation duct line of the liquid medicine circulating between the discharging balloon 3 and the valve 7. Further, the body-insertable device 1 has an imaging unit 8 which images an image for detecting the position relation between the injection needle 4 projected from the casing 2 and a biological tissue surface in the body, a supporting member 9 which supports the imaging unit 8 in a predetermined position at a front end of the casing 2, a control unit 10 which controls driving of the configuring units of the body-insertable device 1, and a power source unit 11 which supplies driving electricity to the control unit 10.

The casing 2 is a capsule-type casing formed in a size which is easy to be introduced into the body and houses the configuring units for realizing the local injection function. The front end of the casing 2 in a longitudinal direction is formed by a dome member 2a having high light transmissivity. The imaging unit 8 is provided in an inner region formed mainly by the dome member 2a.

The discharging balloon 3 is realized by an elastic member such as rubber. The discharging balloon 3 into which the liquid medicine is injected is expanded, and includes the liquid medicine while maintaining the expanded state. The discharging balloon 3 in the expanded state functions to discharge the included liquid medicine by its own latent contracting force. Specifically, the discharging balloon 3 communicates with the valve 7 through the tube 7b and, upon open-driving of the valve 7, is contracted by its own contracting force, and applies a pressure to the liquid medicine to perform the discharging operation of the liquid medicine. The liquid medicine discharged by the discharging balloon 3 sequentially circulates through the tube 7b, the valve 7, and the tube 7a to reach the duct line of the injection needle 4. The liquid medicine then circulates through the duct line of the injection needle 4 to flow out from a tip of the injection needle 4. Upon close-driving of the valve 7, the discharging balloon 3 stops the contraction to stop the discharging operation of the liquid medicine.

Figure 2:
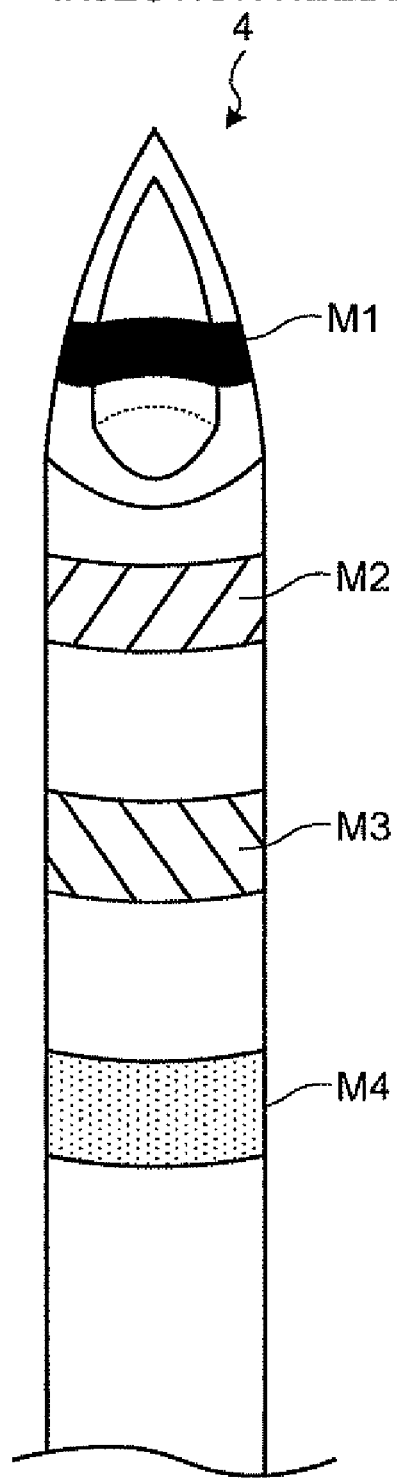
FIG. 2 is a schematic diagram illustrating an example of a plurality of color markers formed on an injection needle.

The injection needle 4 injects the liquid medicine discharged by the discharging balloon 3 into the desired part in the body. Specifically, the injection needle 4 is formed in its inside with the duct line which communicates the tip (pointed side) puncturing the body with a base end, the base end being connected to one end of the tube 7a. The duct line of the injection needle 4 communicates with the valve 7 through the tube 7a. As illustrated in FIG. 2, the injection needle 4 is formed with a plurality of color markers M1 to M4 at predetermined intervals from the tip to the base end. The plurality of color markers M1 to M4 indicate the puncture depth of the injection needle 4. Specifically, the plurality of color markers M1 to M4 are in annular shape continued in a circumferential direction of the injection needle 4, are formed to have a predetermined width in a longitudinal direction of the injection needle 4, and are colored in different colors. It is preferable that the colors of the plurality of color markers M1 to M4 be easy to be distinguished from the biological tissue surface in the body and be, e.g., green, silver, indigo blue, blue, and purple.

The projection mechanism 5 functions as projecting means which projects the injection needle 4 from the casing 2. Specifically, the projection mechanism 5 has a supporting member 5b which supports the injection needle 4, and a linear actuator 5a which functions as a driving unit for projecting or housing the injection needle 4. The linear actuator 5a has a driving shaft connected to the supporting member 5b. The linear actuator 5a moves the supporting member 5b fixed to the injection needle 4 in the longitudinal direction of the injection needle 4. The linear actuator 5a projects the injection needle 4 from the casing 2 or houses the projected injection needle 4 in the casing 2.

The guide member 6 forms the projection opening of the injection needle 4 in the dome member 2a. Specifically, the guide member 6 is a tubular member having high light transmissivity, and has one end fixed to an opening of the dome member 2a and the other end fixed to an opening of the supporting member 9. The guide member 6 forms a path which guides the injection needle 4 to the outside of the casing 2 through the dome member 2a (that is, the projection opening into which the injection needle 4 is inserted).

The valve 7 adjusts the communication state of the discharging balloon 3 and the injection needle 4 through the tubes 7a and 7b, and then starts or stops the discharging operation of the liquid medicine by the discharging balloon 3. Specifically, the valve 7 is open-driven according to control of the control unit 10, and then communicates the discharging balloon 3 with the injection needle 4 through the tubes 7a and 7b. The discharging balloon 3 starts the discharging operation of the liquid medicine. The valve 7 is close-driven according to control of the control unit 10, and then blocks the communication of the discharging balloon 3 with the injection needle 4 through the tubes 7a and 7b. The discharging balloon 3 stops the discharging operation of the liquid medicine.

The imaging unit 8 is typically used for observing a state in the body. When the liquid medicine is injected into the desired part, the imaging unit 8 functions as detecting means which detects the position relation between the injection needle 4 projected from the casing 2 and the biological tissue surface in the body. The imaging unit 8 images an image showing the position relation between the injection needle 4 and the biological tissue surface in the body. Specifically, the imaging unit 8 is realized using an imaging device such as a CCD or CMOS, a light emitting device such as a LED illuminating an imaging field of view of the imaging device, and an optical system such as a lens focusing a reflection light from the imaging field of view onto the imaging device. The imaging unit 8 is fixed to the supporting member 9, and is arranged at the front end of the casing 2 (specifically, an inner space of the dome member 2a) so as to have a predetermined imaging field of view via the dome member 2a or the guide member 6. Specifically, the imaging unit 8 is arranged at the front end of the casing 2 such that the angle formed between its light receiving surface and the longitudinal direction of the casing 2 is a right angle. The angle formed between the light receiving surface of the imaging unit 8 and the longitudinal direction of the injection needle 4 is fixed. The imaging unit 8 has the imaging field of view which at least images a trajectory of the injection needle 4 projected and housed by the projection mechanism 5 (hereinafter, called a projection trajectory). The projection trajectory is formed by a straight line which is extended from the tip of the injection needle 4 housed in the casing 2 in the longitudinal direction of the injection needle 4. The imaging unit 8 can image an image including at least a partial region of the injection needle 4 which is a spatial region between the biological tissue surface such as a digestive tract wall in the body and the casing 2 and is located on the projection trajectory (that is, exposed on the projection trajectory).

The control unit 10 controls driving of the linear actuator 5a, the valve 7 and the imaging unit 8. Specifically, the control unit 10 controls driving of the linear actuator 5a to control the amount of projection of the injection needle 4. The control unit 10 detects the amount of present projection of the injection needle 4 according to driving of the linear actuator 5a. The tip of the injection needle 4 housed in the casing 2 is an origin. The amount of projection of the injection needle 4 is defined by the distance between the tip of the present injection needle 4 projected from the casing 2 (that is, the injection needle 4 located on the projection trajectory) and the origin.

The control unit 10 controls driving of the imaging unit 8 to obtain the image imaged by the imaging unit 8. The control unit 10 obtains, as the image showing the position relation between the biological tissue surface in the body and the injection needle 4, the image including at least the partial region of the injection needle 4 exposed on the projection trajectory from the imaging unit 8. The control unit 10 has an image processing unit 10a which subjects the image imaged by the imaging unit 8 to predetermined image processing. Specifically, the image processing unit 10a detects the color of the color marker (e.g., any one of the color markers M1 to M4) formed on the partial region on the injection needle 4 exposed on the projection trajectory according to the image imaged by the imaging unit 8. The image processing unit 10a detects, from the image, the color of the color marker which is located closest to the tip from the color markers formed on the partial region of the injection needle 4 (that is, the color marker at a distal end which is exposed in a position farthest from the base end of the injection needle 4).

As described above, the plurality of color markers M1 to M4 formed on the injection needle 4 are colored in the colors which are easy to be distinguished from the biological tissue surface in the body. The color markers M1 to M4 form contrast which clarifies the boundary between them and the biological tissue surface in the body in the image imaged by the imaging unit 8. The image processing unit 10a can easily detect the color markers M1 to M4 according to the image imaged by the imaging unit 8.

Here, the control unit 10 knows the present position relation between the biological tissue surface in the body and the injection needle 4 according to the color of the color marker at the distal end detected by the image processing unit 10a. Specifically, the control unit 10 previously stores data indicating the puncture depths of the injection needle 4 corresponding to the colors of the plurality of color markers M1 to M4. The control unit 10 knows the present puncture depth of the injection needle 4 according to the color of the color marker at the distal end detected by the image processing unit 10a. The control unit 10 judges which one of the plurality of color markers M1 to M4 is of the same color as that of the color marker at the distal end. The control unit 10 judges that a puncture depth corresponding to the color marker of the same color as that of the color marker at the distal end is the present puncture depth of the injection needle 4. According to the puncture depth of the injection needle 4 known from the color of the color marker at the distal end, the control unit 10 controls driving of the linear actuator 5a to control the amount of projection of the injection needle 4. The control unit 10 repeatedly controls the amount of projection of the injection needle 4. The control unit 10 controls the present puncture depth of the injection needle 4 to a desired puncture depth, that is, a preferable puncture depth for injecting the liquid medicine into a desired layer in the biological tissue.

The control unit 10 controls driving of the valve 7 to start or stop the discharging operation of the liquid medicine by the discharging balloon 3. Specifically, when controlling the puncture depth of the injection needle 4 to the desired punctuate depth, the control unit 10 controls open-driving of the valve 7 so as to communicate the discharging balloon 3 with the injection needle 4, thereby starting the discharging operation of the liquid medicine by the discharging balloon 3. The control unit 10 controls close-driving of the valve 7 to block the communication of the discharging balloon 3 with the injection needle 4, thereby stopping the discharging operation of the liquid medicine by the discharging balloon 3.

A configuration which defines a timing at which the control unit 10 starts to control driving of the linear actuator 5a may have a timer mechanism or may incorporate a radio receiving mechanism to feed a control signal from the outside to the control unit 10. Each time the control unit 10 controls driving of the linear actuator 5a to move the injection needle 4 by a predetermined unit amount, it repeatedly controls driving of the imaging unit 8. The control unit 10 knows each present puncture depth of the injection needle 4.

Figure 3:
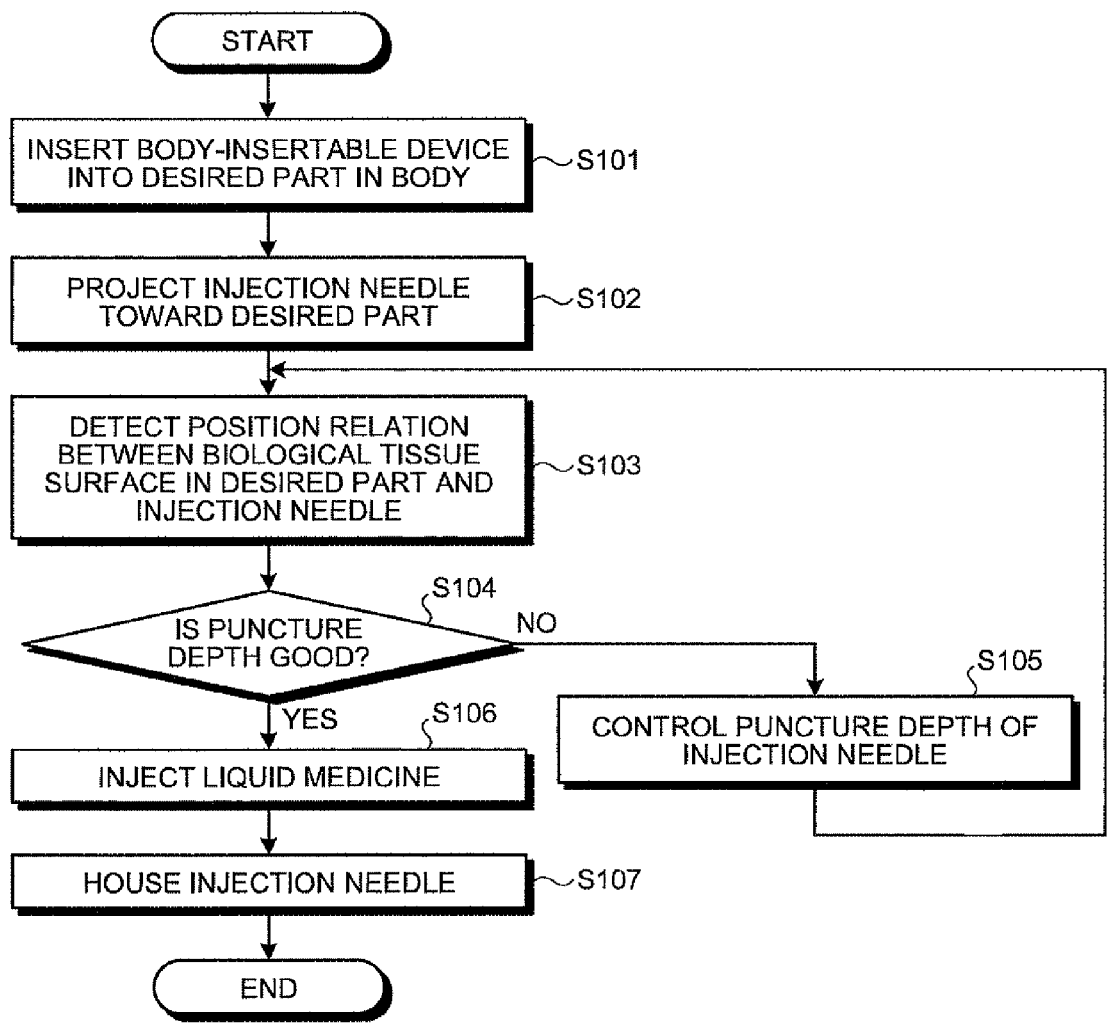
FIG. 3 is a flowchart for explaining a liquid medicine injection method according to the present invention.

The liquid medicine injection method according to the present invention will be described. FIG. 3 is a flowchart for explaining the liquid medicine injection method according to the present invention. The liquid medicine injection method will be described below by illustrating the case in which the liquid medicine is injected into the desired part in the body using the body-insertable device 1 according to the first embodiment.

As illustrated in FIG. 3, the body-insertable device 1 is introduced into the desired part in the body such as a patient (step S101). Specifically, the body-insertable device 1 is introduced into the body from a mouth, and is advanced in an internal organ by peristaltic movement to reach the desired part (affected part) in the body.

The body-insertable device 1 which has reached the desired part in the body through step S101 (inserting step) projects the injection needle 4 toward the desired part in the body (step S102). In step S102 (projecting step), the injection needle 4 projects from the casing 2 of the body-insertable device 1 toward the desired part by driving of the linear actuator 5a according to control of the control unit 10.

The body-insertable device 1 detects the position relation between the biological tissue surface in the desired part in the body and the injection needle 4 (step S103). In step S103 (detecting step), the imaging unit 8 images an image showing the position relation between the biological tissue surface in the desired part and the injection needle 4 on the projection trajectory according to control of the control unit 10. The imaging unit 8 then detects the position relation between the biological tissue surface in the desired part and the injection needle 4. The imaging unit 8 transmits the image showing the position relation to the control unit 10.

The body-insertable device 1 judges whether the puncture depth of the injection needle 4 from the biological tissue surface in the desired part is good or not (step S104). The control unit 10 judges, according to the position relation between the biological tissue surface in the desired part and the injection needle 4 shown by the image obtained from the imaging unit 8, whether the puncture depth of the injection needle 4 is good or not.

The body-insertable device 1 judges that the puncture depth of the injection needle 4 is not good (the puncture depth is shallow or excessively deep) (in step S104, No). The body-insertable device 1 controls the puncture depth of the injection needle 4 so as to be a good puncture depth (step S105). In step S105 (controlling step), the control unit 10 controls the puncture depth of the injection needle 4 from the biological tissue surface according to the position relation between the biological tissue surface and the injection needle 4 detected from the image imaged by the imaging unit 8.

The body-insertable device 1 returns to step 103, and then repeats the processing procedure after step S103. The control unit 10 repeats the processing procedure in steps S103 to S105 to control the puncture depth of the injection needle 4 from the biological tissue surface to the desired punctuate depth.

The body-insertable device 1 judges that the puncture depth of the injection needle 4 is good (the puncture depth is the desired depth) (in step S104, Yes). The body-insertable device 1 injects the liquid medicine into the desired part in the body via the injection needle 4 whose punctuate depth is good (step S106). In step S106, the control unit 10 controls driving of the valve 7 to discharge the liquid medicine in the discharging balloon 3 from the injection needle 4 into the desired part in the body.

The body-insertable device 1 which has injected the liquid medicine into the desired part houses the injection needle 4 puncturing the desired part in the casing 2 (step S107), and then completes this processing procedure. The control unit 10 controls driving of the linear actuator 5a to pull out the injection needle 4 from the desired part, and then houses the pulled-out injection needle 4 in the casing 2.

Figure 4:
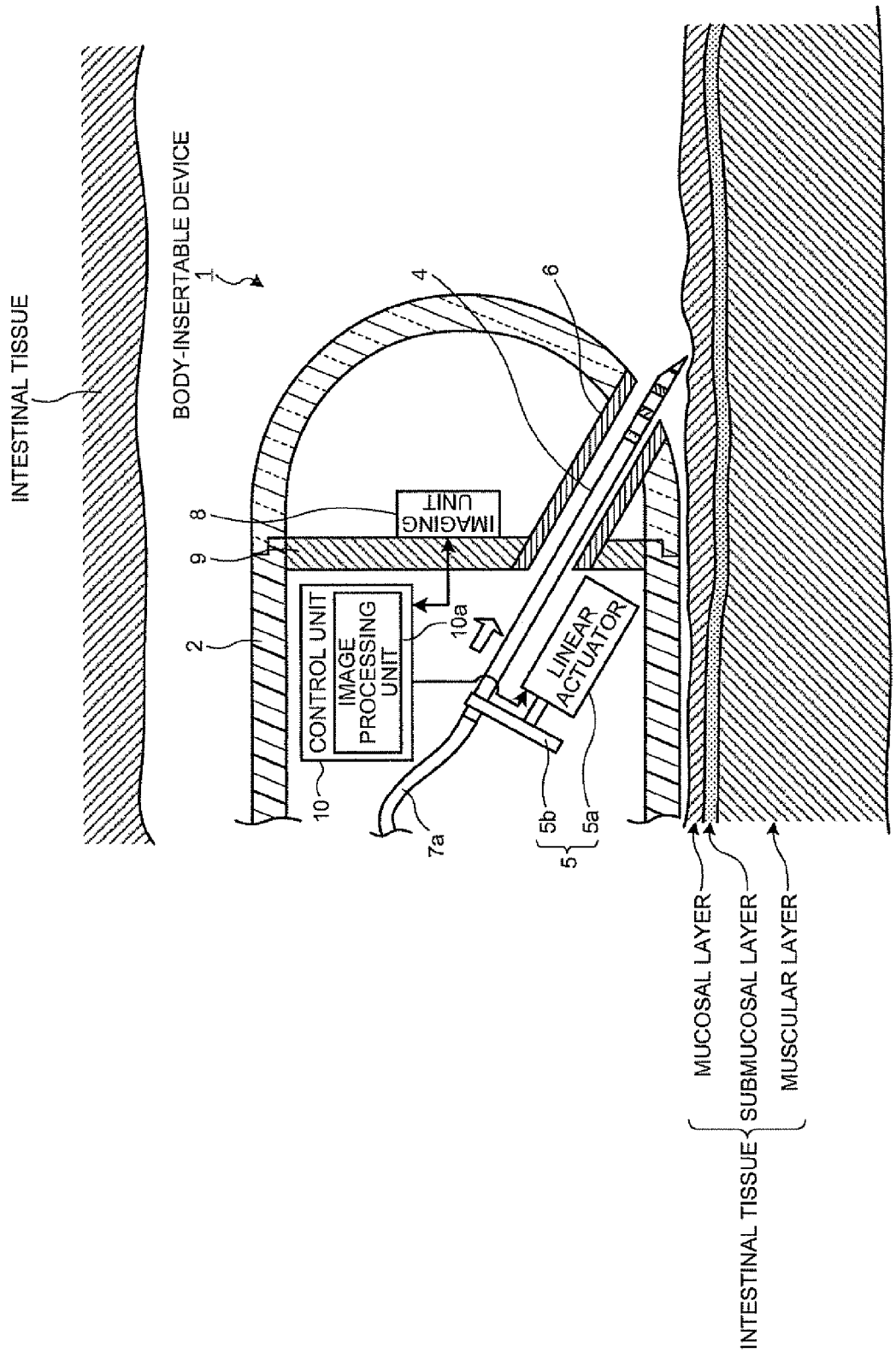
FIG. 4 is a schematic diagram for explaining the operation of a control unit which controls the puncture depth of the injection needle according to the colors of the plurality of color markers.

In steps S101 to S107, the operation of the body-insertable device 1 which controls the puncture depth of the injection needle 4 puncturing the desired part in the body to the desired puncture depth will be specifically described. FIG. 4 is a schematic diagram for explaining the operation of the control unit 10 which controls the puncture depth of the injection needle 4 according to the colors of the plurality of color markers provided on the injection needle 4. The operation of the control unit 10 which controls the puncture depth of the injection needle 4 to the desired punctuate depth will be described below with reference to FIG. 4 by illustrating the case in which the liquid medicine is injected into a submucosal layer of a small intestine which is an example of the desired part in the body.

Figure 5:
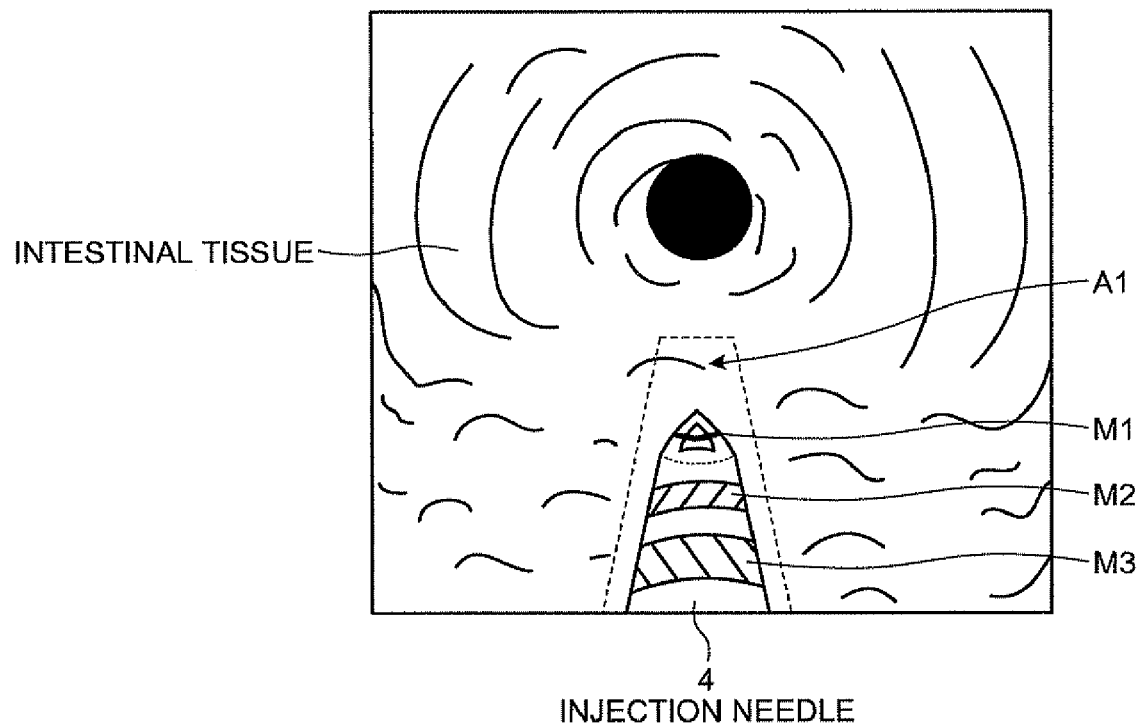
FIG. 5 is a schematic diagram illustrating a specific example of an image including the injection needle in non-puncturing state.

The body-insertable device 1 introduced into the body reaches the desired part in the body, e.g., the small intestine. The control unit 10 controls driving of the linear actuator 5a to project the injection needle 4 from the casing 2 by the predetermined unit amount. The control unit 10 controls driving of the imaging unit 8 to image an image showing the position relation between an intestinal tissue surface in the body and the injection needle 4, thereby obtaining the image from the imaging unit 8. Specifically, as illustrated in FIG. 5, the control unit 10 obtains the image including the injection needle 4 exposed on the projection trajectory from the imaging unit 8. The image processing unit 10a sets a predetermined detection region A1 (a region surrounded by the broken line illustrated in FIG. 5) to the image illustrated in FIG. 5. The image processing unit 10a subjects the detection region A1 to the image processing for detecting the color of the color marker at the distal end.

The detection region A1 set to the image imaged by the imaging unit 8 is an image region set corresponding to the projection trajectory of the injection needle 4. The detection region A1 is also an image region for detecting the color marker on the partial region of the injection needle 4 projected from the casing 2. The partial region of the injection needle 4 exposed on the projection trajectory is included in the detection region A1 of the image obtained from the imaging unit 8. The image processing unit 10a performs the image processing for detecting the color of the color marker from the detection region A1 of the image illustrated in FIG. 5. The image processing unit 10a can detect the color of the color marker M1 at the distal end from the color markers in the partial region of the injection needle 4 exposed on the projection trajectory (e.g., the color markers M1 to M3).

The control unit 10 knows, according to the color of the color marker M1 at the distal end detected by the image processing unit 10a, that the present position relation between the intestinal tissue surface in the body and the injection needle 4 is a position relation in non-puncturing state. The position relation in non-puncturing state means a position relation in which the puncture depth of the injection needle 4 puncturing the biological tissue in the body is substantially zero. The position relation in non-puncturing state includes a position relation in which the tip of the injection needle 4 is not touching the biological tissue surface in the body (that is, the injection needle 4 does not puncture the biological tissue). The position relation in non-puncturing state also includes a position relation in which part of a duct line opening at the tip of the injection needle 4 is exposed on the biological tissue surface (that is, the liquid medicine discharged via the injection needle 4 is leaked onto the biological tissue surface).

Figure 6:
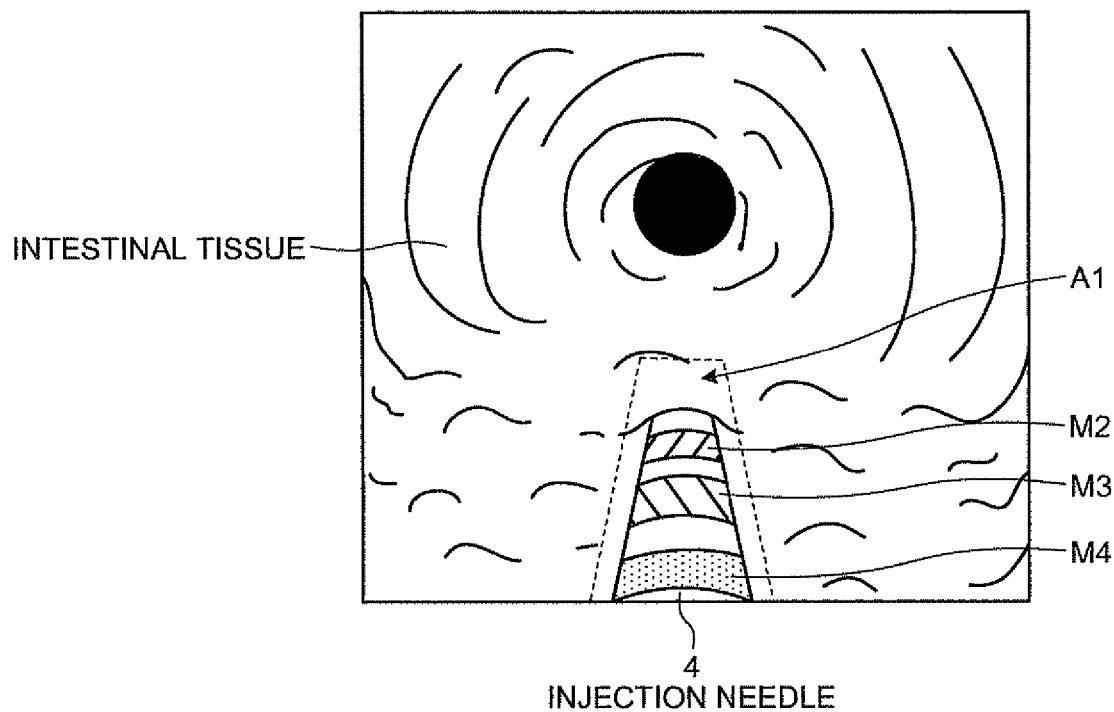
FIG. 6 is a schematic diagram illustrating a specific example of an image including the injection needle which shallowly punctures a biological tissue.

The present position relation between the injection needle 4 and the biological tissue surface is the position relation in non-puncturing state. In this case, the control unit 10 controls driving of the linear actuator 5a to move the injection needle 4 by the predetermined unit amount in a direction projected from the casing 2 (projecting direction). At the same time, the control unit 10 controls driving of the imaging unit 8 to obtain an image showing the position relation between the moved injection needle 4 and the intestinal tissue surface. Specifically, as illustrated in FIG. 6, the control unit 10 obtains an image showing the state in which the injection needle 4 punctures the intestinal tissue to the region at its tip from the color marker M2. The image processing unit 10a sets the detection region A1 to the image illustrated in FIG. 6. The image processing unit 10a performs the image processing for detecting the colors of the color markers included in the detection region A1. The image processing unit 10a detects the color of the color marker M2 at the distal end from among the color markers in the partial region of the injection needle 4 exposed on the projection trajectory (e.g., the color markers M2 to M4).

According to the color of the color marker M2 at the distal end detected by the image processing unit 10a, the control unit 10 knows that the present position relation between the intestinal tissue surface in the body and the injection needle 4 is a position relation in puncturing state and that the puncture depth of the injection needle 4 is insufficient (shallow). The position relation in puncturing state means a position relation in which the injection needle 4 punctures the biological tissue in the body. The position relation in puncturing state is, e.g., a position relation in which the duct line opening at the tip of the injection needle 4 is under the biological tissue surface. As illustrated in FIG. 4, the intestinal tissue in the body is formed mainly by a mucosal layer which forms an inner wall surface of a digestive tract, a submucosal layer formed under the mucosal layer, and a muscular layer as a muscular tissue layer of an intestine. In particular, the submucosal layer is a thin layer formed between the mucosal layer and the muscular layer of the intestinal tissue. The body-insertable device 1 injects the liquid medicine into the submucosal layer via the injection needle 4. In this case, the puncture depth of the injection needle 4 puncturing the mucosal layer of the intestinal tissue is shallow and insufficient, as judged by the control unit 10 according to the color of the color marker M2 at the distal end.

Figure 7:
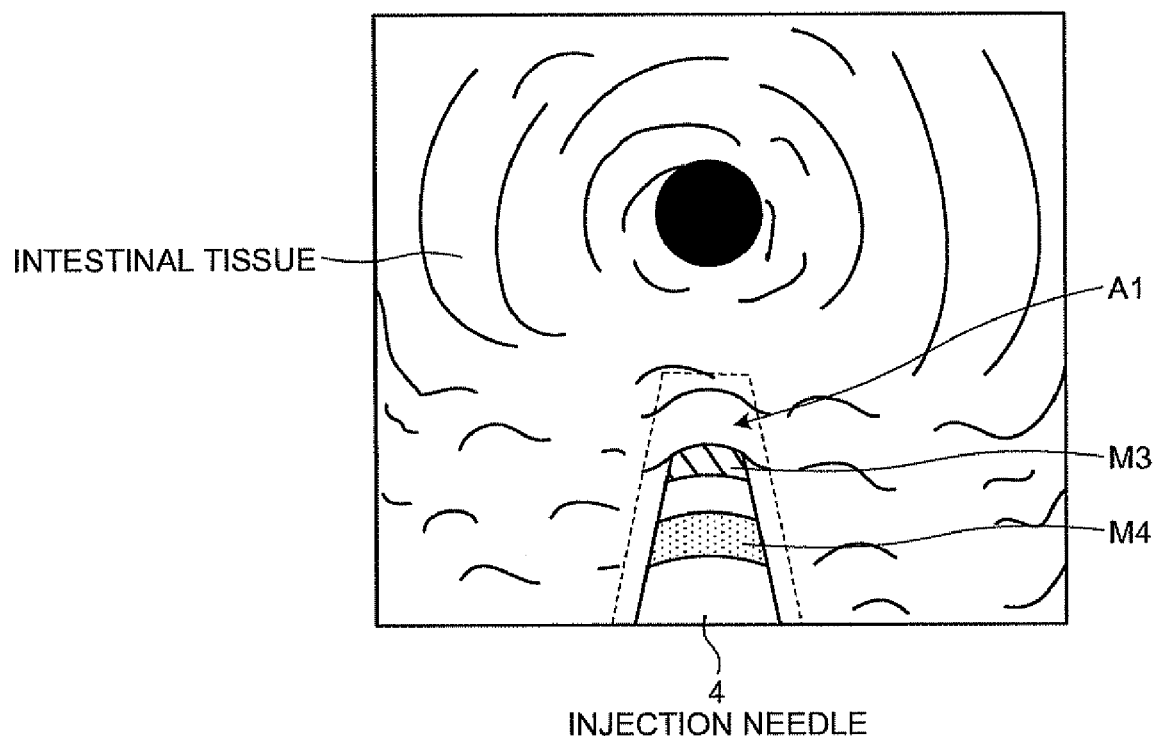
FIG. 7 is a schematic diagram illustrating a specific example of an image including the injection needle which punctures the biological tissue to a desired puncture depth.

The puncture depth of the injection needle 4 is shallow. The control unit 10 controls driving of the linear actuator 5a to move the injection needle 4 by the predetermined unit amount in the projecting direction. At the same time, the control unit 10 controls driving of the imaging unit 8 to obtain an image showing the position relation between the moved injection needle 4 and the intestinal tissue surface. Specifically, as illustrated in FIG. 7, the control unit 10 obtains an image showing the state in which the injection needle 4 punctures the intestinal tissue to the region at the tip as compared to the color marker M3. The image processing unit 10a sets the detection region A1 to the image illustrated in FIG. 7. The image processing unit 10a performs the image processing which detects the colors of the color markers included in the detection region A1. The image processing unit 10a detects the color of the color marker M3 at the distal end from the color markers in the partial region of the injection needle 4 exposed on the projection trajectory (e.g., the color markers M3 and M4).

According to the color of the color marker M3 at the distal end detected by the image processing unit 10a, the control unit 10 knows that the present position relation between the intestinal tissue surface in the body and the injection needle 4 is the position relation in puncturing state and that the puncture depth of the injection needle 4 is the desired depth (the injection needle 4 precisely punctures the submucosal layer).

Figure 8:
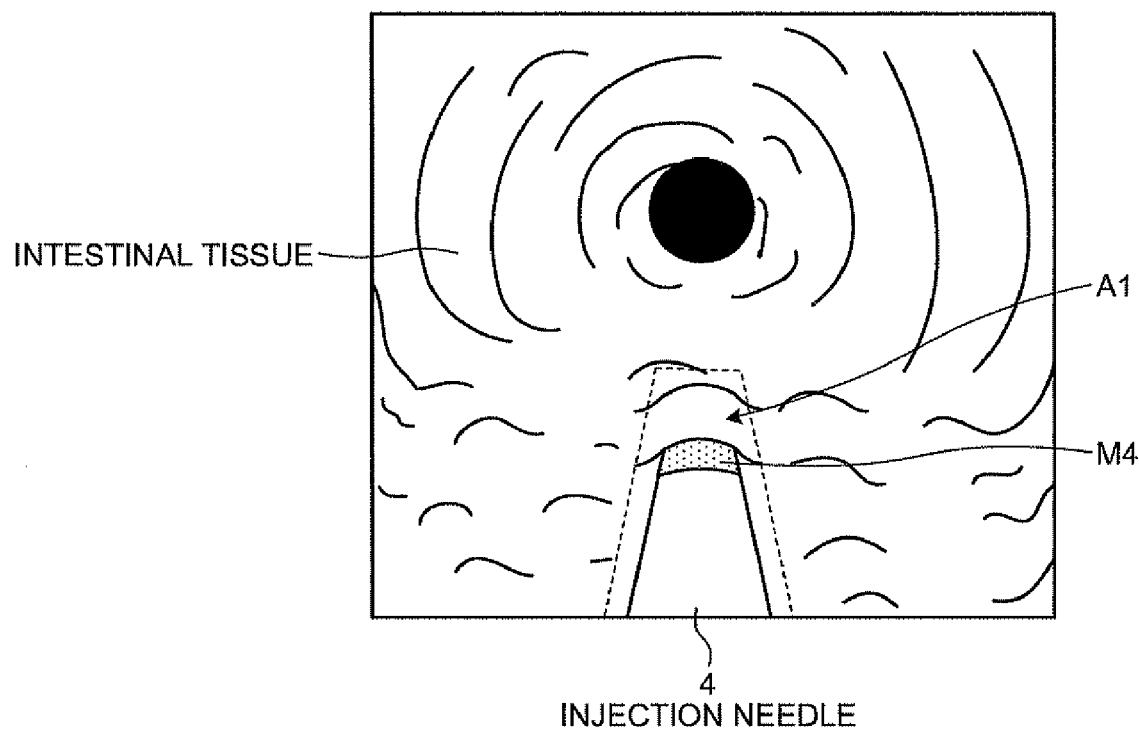
FIG. 8 is a schematic diagram illustrating a specific example of an image including the injection needle which punctures the biological tissue excessively deeply.

As illustrated in FIG. 8, the control unit 10 obtains an image showing the state in which the injection needle 4 punctures the intestinal tissue to the region at the tip as compared to the color marker M4. According to the color of the color marker M4 at the distal end detected from the image, the control unit 10 knows that the present position relation between the intestinal tissue surface in the body and the injection needle 4 is the position relation in puncturing state. The control unit 10 also knows that the puncture depth of the injection needle 4 is excessive (the injection needle 4 punctures the muscular layer through the submucosal layer). The image processing unit 10a sets the detection region A1 to the image illustrated in FIG. 8. The image processing unit 10a performs the image processing which detects the color of the color marker included in the detection region A1. The image processing unit 10a detects the color of the color marker M4 at the distal end from the color markers in the partial region of the injection needle 4 exposed on the projection trajectory.

The puncture depth of the injection needle 4 is excessively deep. The control unit 10 controls driving of the linear actuator 5a to return the injection needle 4 by the predetermined unit amount in a direction housing the injection needle 4 in the casing 2 (housing direction). At the same time, the control unit 10 controls driving of the imaging unit 8 to obtain an image showing the position relation between the moved injection needle 4 and the intestinal tissue surface.

Figure 9:
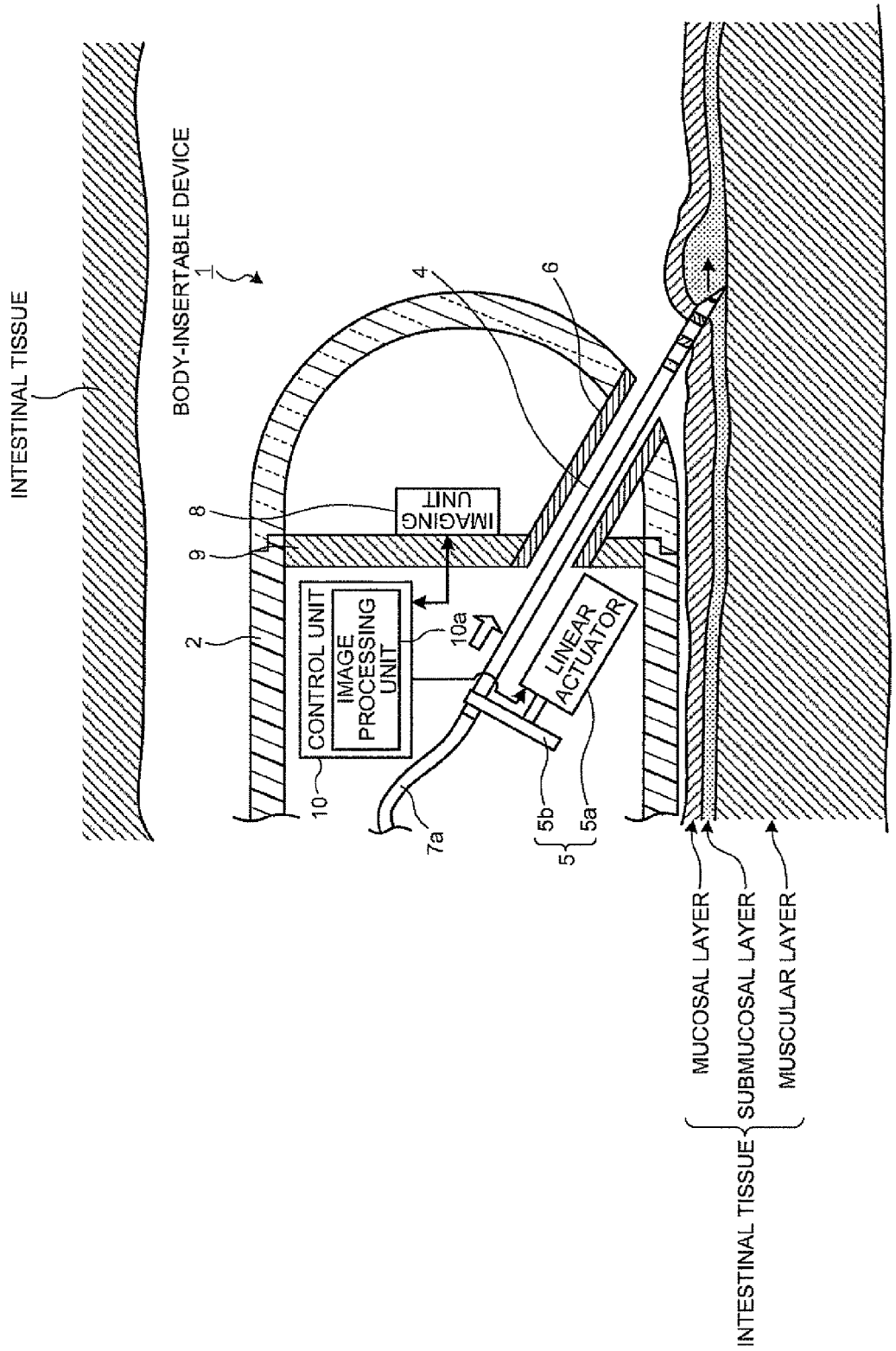
FIG. 9 is a schematic diagram illustrating the state in which the injection needle punctures an intestinal tissue to the depth of a submucosal layer.

The control unit 10 repeatedly controls driving of the linear actuator 5a and the imaging unit 8. The control unit 10 thereby moves the injection needle 4 by the predetermined unit amount in the projecting direction or the housing direction. The control unit 10 monitors the position relation between the intestinal tissue surface and the injection needle 4 and the puncturing state of the injection needle 4. The control unit 10 controls the amount of projection of the injection needle 4. The control unit 10 gradually moves the tip of the injection needle 4 from the intestinal tissue surface toward the layer at the desired depth. The control unit 10 can control the puncture depth of the injection needle 4 from the intestinal tissue surface to the desired puncture depth. As illustrated in FIG. 9, the control unit 10 can finely adjust the puncture depth of the injection needle 4 so as to precisely locate the duct line opening at the tip of the injection needle 4 into the submucosal layer of the intestinal tissue.

The control unit 10 injects the liquid medicine into the submucosal layer via the injection needle 4 whose puncture depth from the intestinal tissue surface is controlled to the desired puncture depth. The control unit 10 controls open-driving of the valve 7 to communicate the discharging balloon 3 with the injection needle 4. The discharging balloon 3 starts the discharging operation of the liquid medicine according to control of the control unit 10. The discharging balloon 3 discharges the liquid medicine into the duct line of the injection needle 4 through the tubes 7a and 7b and the valve 7. The liquid medicine discharged by the discharging balloon 3 is precisely injected into the submucosal layer via the injection needle 4. The state in which the liquid medicine is injected into the submucosal layer is continued until the contraction force of the discharging balloon 3 is zero or until the valve 7 is close-driven according to control by the control unit 10. A predetermined amount of the liquid medicine can be injected into the part at the desired puncture depth in the body, such as the submucosal layer.

Injection of the liquid medicine into the submucosal layer is completed. The control unit 10 controls driving of the linear actuator 5a to move the injection needle 4 in the housing direction. The control unit 10 then pulls out the injection needle 4 from the intestinal tissue to house the injection needle 4 in the casing 2. The control unit 10 need not allow the imaging unit 8 to image an image showing the position relation between the intestinal tissue surface and the injection needle 4. The body-insertable device 1 which houses the injection needle 4 in the casing 2 can move in the digestive tract in the body without puncturing other parts in the body with no intention.

The image processing unit 10a detects the color of the color marker at the distal end in the partial region of the injection needle 4 exposed on the projection trajectory. In this case, the image processing unit 10a may sequentially detect the color of one or more color markers included in the detection region A1 from the base end to the tip of the injection needle 4. Then, the image processing unit 10a may detect the color of the color marker detected last as the color of the color marker at the distal end. In addition, the image processing unit 10a may previously store an arrangement of the plurality of color markers (e.g., the color markers M1 to M4) formed on the injection needle 4. Then, the image processing unit 10a may detect all the color markers included in the detection region A1 to judge the color marker which cannot be detected from the detection region A1 (that is, the buried color marker hidden under the biological tissue surface by puncturing the biological tissue via the injection needle 4). Finally, the image processing unit 10a may detect, as the color of the color marker at the distal end, the color of the color marker adjacent to the buried color marker on the base end of the injection needle 4 from all the color markers detected from the detection region A1.

As described above, in the first embodiment of the present invention, the body-insertable device 1 has the above configuration. The puncture depth of the injection needle which punctures the desired part in the body can be easily adjusted to the desired depth from the biological tissue surface. When the liquid medicine is injected into the thin layer such as the submucosal layer of the intestinal tissue, the tip of the injection needle can be precisely located into the thin layer. The body-insertable device which can inject the liquid medicine into the biological tissue to the desired puncture depth can be realized.

The injection needle which has injected the liquid medicine into the desired part in the body is housed in the casing. When being moved in the body after injection of the liquid medicine, the injection needle can be prevented from puncturing other parts in the body with no intention.

Open- and close-driving of the valve is controlled by the control unit to start or stop the discharging operation of the liquid medicine. Start and stop of the discharging operation of the liquid medicine can be repeated at the desired timing. The discharging operation of the liquid medicine can be intermittently repeated since the body-insertable device is introduced into the body until it is discharged to the outside. A desired amount of the liquid medicine can be injected into a plurality of desired parts in the body.

A second embodiment of the present invention will be described. In the first embodiment, the amount of projection of the injection needle is controlled according to the color of the color marker indicating the puncture depth of the injection needle, and the puncture depth of the injection needle from the biological tissue surface is controlled. In the second embodiment, the puncture angle of the injection needle is detected according to a figure of the color marker located near the puncturing portion of the injection needle which punctures the biological tissue, and the amount of projection of the injection needle is controlled corresponding to the detected puncture angle.

Figure 10:
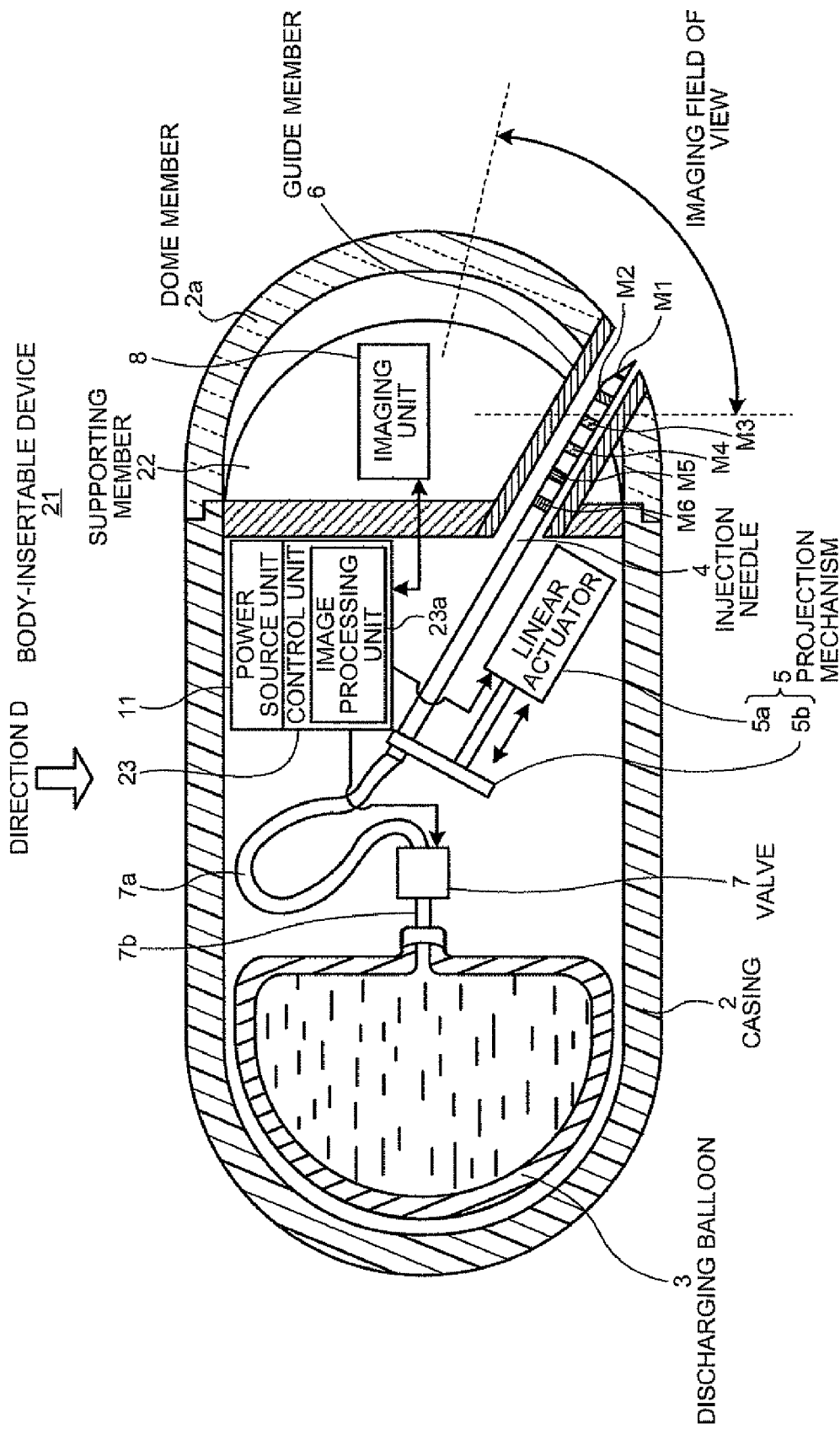
FIG. 10 is a sectional schematic diagram schematically illustrating a configuring example of a body-insertable device according to the second embodiment of the present invention.
Figure 11:
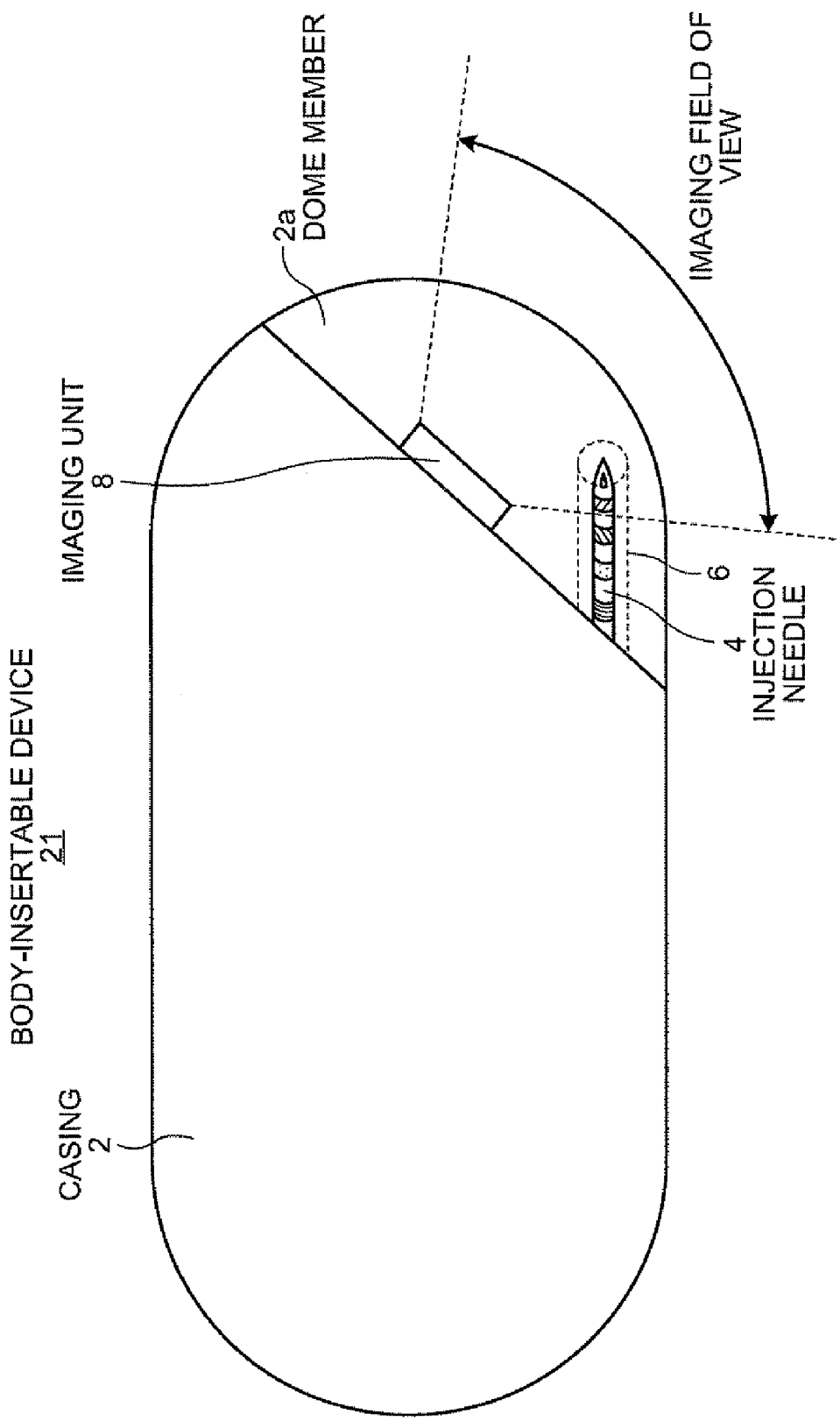
FIG. 11 is an appearance schematic diagram of the body-insertable device illustrated in FIG. 10, seen from its side surface in a direction D.

FIG. 10 is a sectional schematic diagram schematically illustrating a configuration example of a body-insertable device according to the second embodiment of the present invention. FIG. 11 is an appearance schematic diagram of the body-insertable device illustrated in FIG. 10, seen from its side surface in a direction D. As illustrated in FIG. 10, a body-insertable device 21 has a supporting member 22 in place of the supporting member 9 of the body-insertable device 1 according to the first embodiment, and a control unit 23 in place of the control unit 10. The injection needle 4 has additionally color markers M5 and M6 formed at predetermined intervals at the base end of the injection needle 4 as compared to the color marker M4. The color markers M1 to M6 are formed so as to have a predetermined width in the longitudinal direction of the injection needle 4. The colors of the color markers M1 to M6 are colors which are easy to be distinguished from the biological tissue surface in the body, and are different from each other. Other configuration is the same as that of the first embodiment. The same configuring parts are indicated by similar reference numerals, and the description is omitted.

Figure 12:
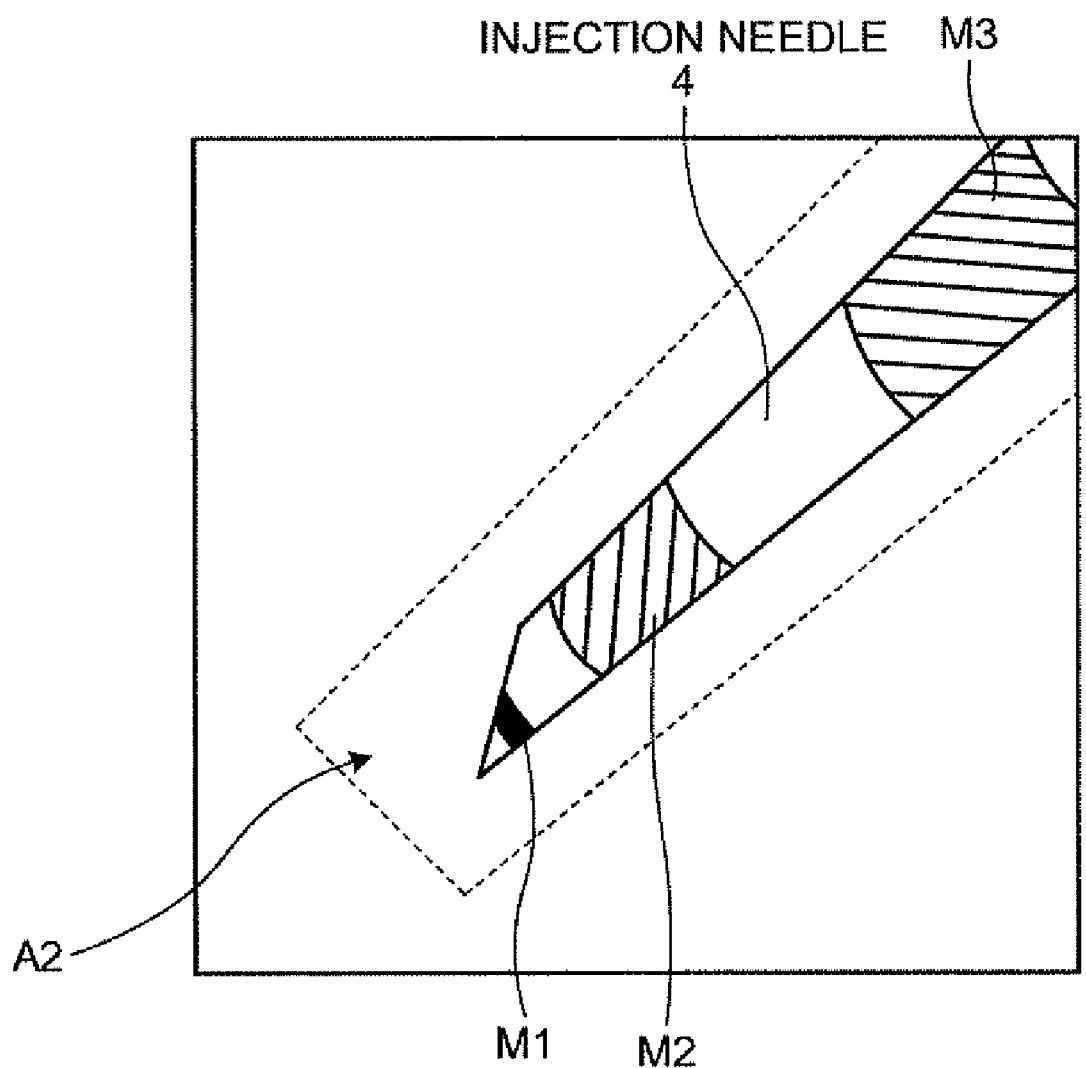
FIG. 12 is a schematic diagram illustrating a specific example of an image which images the injection needle in a substantially transverse direction.

The supporting member 22 supports the imaging unit 8 tilted with respect to the longitudinal direction of the casing 2 such that the imaging unit 8 can have the imaging field of view which can image the injection needle 4 in a substantially transverse direction. Specifically, as illustrated in FIG. 11, the supporting member 22 is fixed to the front end of the casing 2 and supports the imaging unit 8 tilted such that the angle formed between a center axis of the imaging field of view of the imaging unit 8 (e.g., an optical axis of the imaging unit 8) and an axis of the injection needle 4 in the longitudinal direction is a predetermined angle. As illustrated in FIG. 12, the imaging unit 8 supported by the supporting member 22 can image an image of the partial region of the injection needle 4 exposed on the projection trajectory in the substantially transverse direction.

In substantially the same manner as that of the control unit 10 of the body-insertable device 1 according to the first embodiment, the control unit 23 functions to control driving of the linear actuator 5a, the imaging unit 8, and the valve 7. Specifically, the control unit 23 controls driving of the valve 7 to start or stop the discharging operation of the liquid medicine by the discharging balloon 3. The control unit 23 controls driving of the linear actuator 5a and the imaging unit 8 at substantially the same timing as that of the control unit 10. The control unit 23 obtains an image showing the position relation between the biological tissue surface in the body and the injection needle 4 each time the injection needle 4 is moved by the predetermined unit amount, e.g., an image of the injection needle 4 exposed on the projection trajectory as illustrated in FIG. 12 in the substantially transverse direction.

The control unit 23 has an image processing unit 23a in place of the image processing unit 10a of the control unit 10. In substantially the same manner as that of the image processing unit 10a, the image processing unit 23a detects the color of the color marker at the distal end according to the image imaged by the imaging unit 8. As illustrated in FIG. 12, the image processing unit 23a sets a detection region A2 (a region surrounded by the broken line illustrated in FIG. 12) corresponding to the partial region of the injection needle 4 exposed on the projection trajectory. The image processing unit 23a detects the color of the color marker at the distal end located at the tip of the injection needle from the color markers included in the detection region A2.

In substantially the same manner as that of the detection region A1 according to the first embodiment, the detection region A2 is an image region which detects the color marker on the partial region of the injection needle 4. The detection region A2 is also set corresponding to the partial region of the injection needle 4 seen in a direction substantially perpendicular to the longitudinal direction of the injection needle 4 (that is, in the substantially transverse direction with respect to the injection needle 4). The partial region of the injection needle 4 imaged by the imaging unit 8 in the substantially transverse direction is included in the detection region A2 of the image obtained from the imaging unit 8.

The injection needle 4 punctures the biological tissue in the body. The image processing unit 23a detects, from the detection region A2, the partial region of the injection needle 4 in puncturing state, that is, the color marker exposed near the biological tissue surface from the color markers in the partial region exposed on the projection trajectory (the color marker near the puncturing portion). The image processing unit 23a calculates the puncture angle of the injection needle 4 with respect to the biological tissue surface according to the figure formed by the color marker near the puncturing portion.

According to the color of the color marker at the distal end and the puncture angle of the injection needle 4 obtained by the image processing unit 23a, the control unit 23 controls driving of the linear actuator 5a to control the amount of projection of the injection needle 4. The control unit 23 then controls the puncture depth of the injection needle 4 puncturing the biological tissue so as to be the desired puncture depth. According to the color of the color marker at the distal end, the control unit 23 knows the position relation between the injection needle 4 and the biological tissue surface. The control unit 23 controls the amount of projection of the injection needle 4 corresponding to the puncture angle with respect to the biological tissue surface. Specifically, the control unit 23 judges, according to the color of the color marker at the distal end, that the position relation is in non-puncturing state or in puncturing state. In the case of the position relation in puncturing state, the control unit 23 judges the degree of the puncture depth of the injection needle 4 according to the color of the color marker at the distal end and the puncture angle of the injection needle 4. The amount of projection of the injection needle 4 necessary for controlling the puncture depth from the biological tissue surface to the desired puncture depth is changed according to the puncture angle of the injection needle 4 with respect to the biological tissue surface. Specifically, the amount of projection of the injection needle 4 necessary for the control is decreased as the puncture angle of the injection needle 4 is close to a right angle from 0°, and is increased as the puncture angle of the injection needle 4 is acute. The control unit 23 controls the amount of projection of the injection needle 4 according to the judged position relation between the biological tissue surface and the injection needle 4 and degree of the puncture depth of the injection needle 4. Thus, the control unit 23 can control the puncture depth of the injection needle 4 to the desired puncture depth at high accuracy.

The color marker M1 is the color marker at the distal end. The control unit 23 knows that the injection needle 4 does not puncture the biological tissue surface. The control unit 23 controls driving of the linear actuator 5a as in the control unit 10 without depending on the penetrating angle of the injection needle 4 into the biological tissue surface. The control unit 23 moves the injection needle 4 in the projecting direction until the position relation between the injection needle 4 and the biological tissue surface becomes the position relation in puncturing state. Until the injection needle 4 punctures the biological tissue, the image processing unit 23a needs not calculate the puncture angle of the injection needle 4.

Figure 13:
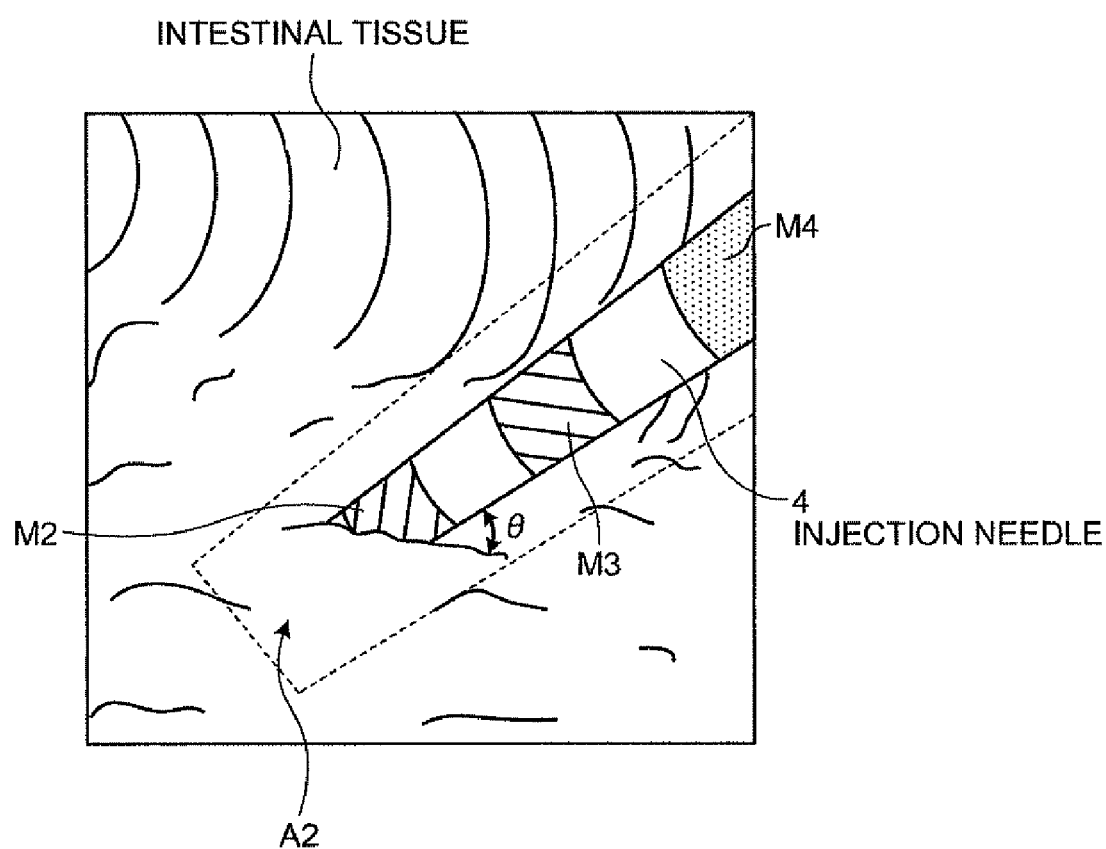
FIG. 13 is a schematic diagram illustrating a specific example of an image which images the injection needle puncturing the intestinal tissue in the substantially transverse direction.

The operation of the body-insertable device 21 which controls the puncture depth of the injection needle 4 which punctures the desired part in the body to the desired puncture depth will be specifically described. FIG. 13 is a schematic diagram illustrating an example of an image which images the injection needle 4 which punctures the desired part in the body. The operation of the control unit 23 which controls the puncture depth of the injection needle 4 to the desired puncture depth at high accuracy will be described below by illustrating the case in which the liquid medicine is injected into the submucosal layer of the small intestine which is an example of the desired part in the body.

In step S103 of the processing procedure in steps S101 to S107 (see FIG. 3), the body-insertable device 21 detects the position relation between the injection needle 4 and the biological tissue surface and the puncture angle of the injection needle 4 with respect to the biological tissue surface according to the image which images the injection needle 4 on the projection trajectory in the substantially transverse direction. In step S105, the body-insertable device 21 controls the puncture depth of the injection needle 4 from the biological tissue surface to the desired puncture depth according to the position relation between the injection needle 4 and the biological tissue surface and the necessary amount of projection of the injection needle 4 changed according to the puncture angle of the injection needle 4. The remaining procedure (steps S101, S102, S104, S106, and S107) of the body-insertable device 21 is the same as that of the first embodiment.

The body-insertable device 21 introduced into the body reaches the desired part, e.g., the small intestine, in the body. The control unit 23 repeatedly controls driving of the linear actuator 5a and the imaging unit 8 in substantially the same manner as that of the first embodiment until the injection needle 4 punctures the intestinal tissue (that is, the position relation in puncturing state). Specifically, until the image processing unit 23a detects, as the color of the color marker at the distal end, the color of the color marker M2 from the detection region A2 of the image illustrated in FIG. 12, the control unit 23 repeatedly controls driving of the linear actuator 5a and the imaging unit 8 in substantially the same manner as that of the control unit 10 of the body-insertable device 1 according to the first embodiment.

The injection needle 4 punctures the intestinal tissue. The control unit 23 controls driving of the imaging unit 8. As illustrated in FIG. 12, the control unit 23 obtains the image which images the injection needle 4 puncturing the intestinal tissue. The image processing unit 23a detects the color of the color marker M2 at the distal end from the color markers included in the detection region A2. The image processing unit 23a detects a figure formed by the color marker M2 near the puncturing portion from the color markers included in the detection region A2. The image processing unit 23a calculates, according to the figure of the color marker M2 near the puncturing portion, the angle formed between the intestinal tissue surface and the injection needle 4, that is, a puncture angle θ of the injection needle 4 with respect to the intestinal tissue.

Figure 14:
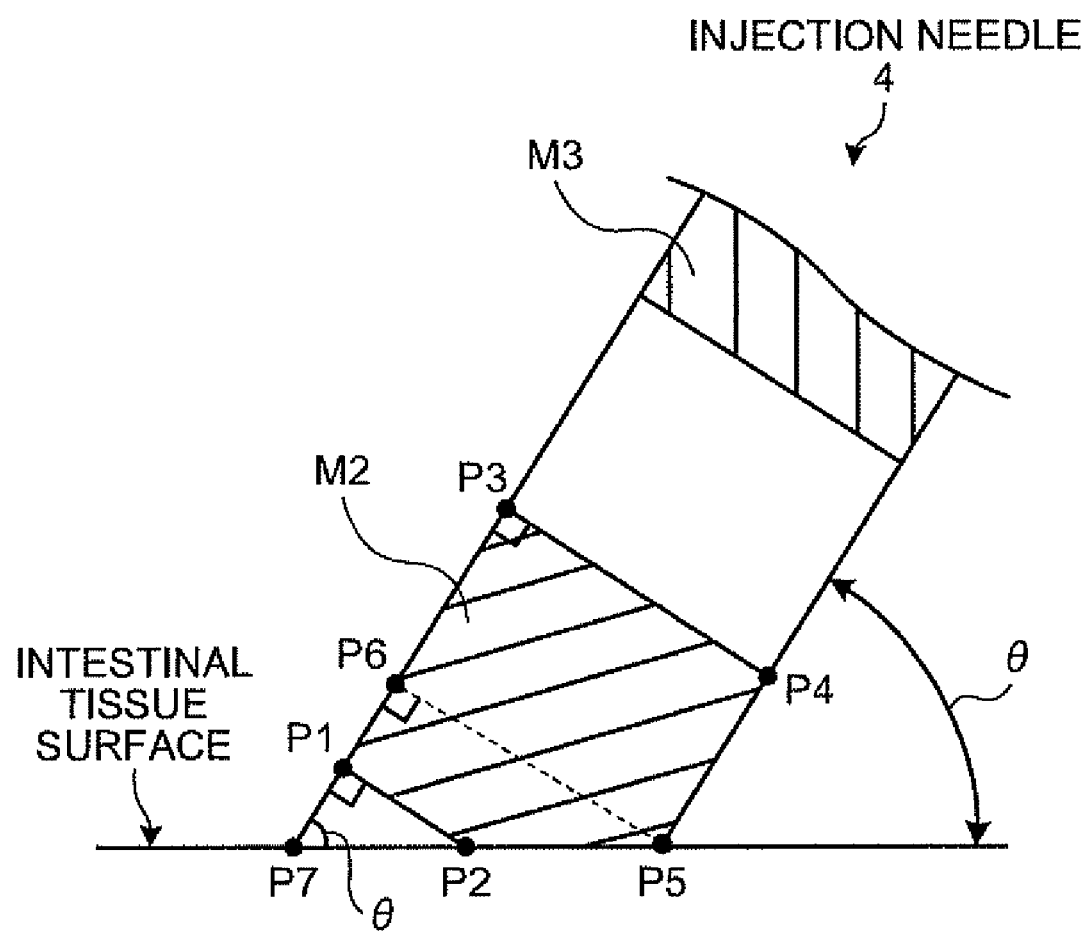
FIG. 14 is a schematic diagram for explaining processing of an image processing unit which calculates the puncture angle of the injection needle with respect to a biological tissue surface.

Processing of the image processing unit 23a which calculates the puncture angle of the injection needle 4 will be described here. FIG. 14 is a schematic diagram for explaining the processing of the image processing unit 23a which calculates the puncture angle of the injection needle 4 with respect to the biological tissue surface. FIG. 14 schematically illustrates the vicinity of the puncturing portion of the injection needle 4 illustrated in FIG. 13. The injection needle 4 illustrated in FIG. 14 forms the puncture angle θ with respect to the intestinal tissue surface.

The image processing unit 23a detects the figure formed by the color marker M2 near the puncturing portion from the detection region A2 of the image illustrated in FIG. 13. As illustrated in FIG. 14, the image processing unit 23a detects, as the figure of the color marker M2 near the puncturing portion, a polygon having five apexes P1 to P5. The image processing unit 23a calculates the lengths of sides of the polygon by the color marker M2 according to the image illustrated in FIG. 13. The image processing unit 23a calculates the puncture angle θ of the injection needle 4 according to the obtained lengths of the sides.

Specifically, the image processing unit 23a calculates the lengths of a side P1P2 and a side P4P5 exposed in positions nearest the intestinal tissue surface in the polygon by the color marker M2. The image processing unit 23a calculates the length of a side P3P4 substantially parallel with the side P1P2 and the length of a side P1P3 substantially parallel with the side P4P5. The side P1P3 is substantially perpendicular to the side P1P2 and the side P3P4. The image processing unit 23a sets a segment P5P6 which is parallel with the side P3P4 and connects the apex P5 and the side P1P3. The length of the segment P5P6 is substantially the same as that of the side P3P4. The length of a segment P1P6 is obtained by subtracting the length of the side P4P5 from the length of the side P1P3. Here, an apex P7 is a point of intersection of an extension line of the side P1P3 and the intestinal tissue surface (a point on the boundary between the injection needle 4 puncturing the intestinal tissue and the intestinal tissue surface). A right-angled triangle having the apexes P5, P6, and P7 is similar to a right-angled triangle having the apexes P2, P1, and P7. According to these, the image processing unit 23a can calculate the angle formed between a side P5P7 and a side P6P7 of the right-angled triangle having the apexes P5, P6, and P7, that is, the puncture angle θ of the injection needle 4.

The angle formed between the center axis of the imaging field of view of the imaging unit 8 and the longitudinal axis of the injection needle 4 is not 90°. In this case, the image processing unit 23a may convert the figure by the color marker near the puncturing portion to a figure seen in a direction at an angle of 90° with respect to the axis of the injection needle 4 in the longitudinal direction. Then, the image processing unit 23a may use the lengths of sides of the converted figure to calculate the puncture angle θ.

According to the puncture angle θ calculated by the image processing unit 23a and the color of the color marker at the distal end, the control unit 23 controls driving of the linear actuator 5a to control the amount of projection of the injection needle 4. The control unit 23 controls the puncture depth of the injection needle 4 from the biological tissue surface to the desired puncture depth. The control unit 23 switches, as the color of the color marker at the distal end which is judged to be the desired puncture depth, between the color markers M2 to MG corresponding to the puncture angle θ calculated by the image processing unit 23a. The control unit 23 controls the amount of projection of the injection needle 4.

Specifically, when the body-insertable device 21 injects the liquid medicine into the submucosal layer of the intestinal tissue, the amount of projection of the injection needle 4 necessary for it to penetrate through the mucosal layer to reach the submucosal layer (that is, a distance in which the injection needle 4 passes through the mucosal layer) is decreased as the puncture angle θ of the injection needle 4 with respect to the intestinal tissue surface is close to a right angle from 0°, and is increased as it is acute. In puncturing state in which the puncture angle θ is 45°, the control unit 23 performs driving control in which the injection needle 4 punctures the intestinal tissue to the position of the color marker M4 (that is, the color marker M4 is the color marker at the distal end). The puncture depth of the injection needle 4 can be thus matched with the submucosal layer. When the puncture angle θ calculated by the image processing unit 23a is smaller than 45°, the control unit 23 performs driving control in which the color marker M5 is the color marker at the distal end, thereby increasing the amount of projection of the injection needle 4 into the intestinal tissue. When the puncture angle θ is near 0°, the control unit 23 performs driving control in which the color marker M6 is the color marker at the distal end, thereby increasing the amount of projection of the injection needle 4. When the puncture angle θ calculated by the image processing unit 23a is larger than 45°, the control unit 23 performs driving control in which the color marker M3 is the color marker at the distal end, thereby decreasing the amount of projection of the injection needle 4 into the intestinal tissue. When the puncture angle θ is near 90°, the control unit 23 performs driving control in which the color marker M2 is the color marker at the distal end, thereby decreasing the amount of projection of the injection needle 4.

The digestive tract into which the body-insertable device 21 is introduced has curved points in the body. An inner wall surface of the digestive tract has many portions in uneven shape. The puncture angle θ when the injection needle 4 punctures the biological tissue is often different according to the puncture position of the biological tissue by the injection needle 4 even in the same digestive tract. As described above, the control unit 23 controls the amount of projection of the injection needle 4 corresponding to the puncture angle θ. When the puncture angle θ of the injection needle 4 is changed according to the puncture position of the biological tissue, the control unit 23 can reliably control the puncture depth of the injection needle 4 from the biological tissue surface to the desired puncture depth (that is, the preferable puncture depth for injecting the liquid medicine into the desired layer in the biological tissue).

As described above, in the second embodiment of the present invention, the body-insertable device 21 has the above configuration. When the angle formed between the projection trajectory of the injection needle and the biological tissue surface is different according to the puncture position of the biological tissue, the amount of projection of the injection needle can be controlled at high accuracy such that the injection needle punctures the biological tissue to the desired puncture depth. The body-insertable device which can have the same operation and effect as those of the first embodiment and control the puncture depth of the injection needle from the biological tissue surface to the desired puncture depth without depending on the puncture angle can be realized.

A third embodiment of the present invention 3 will be described. In the second embodiment, the puncture angle θ of the injection needle 4 is calculated according to the figure formed by the color marker near the puncturing portion of the injection needle 4. In the third embodiment, a ring marker is slidably attached to the tip of the injection needle 4 such that its angle can be changed with respect to the longitudinal direction, and the puncture angle θ of the injection needle 4 is calculated according to an image which images the ring marker.

Figure 15:
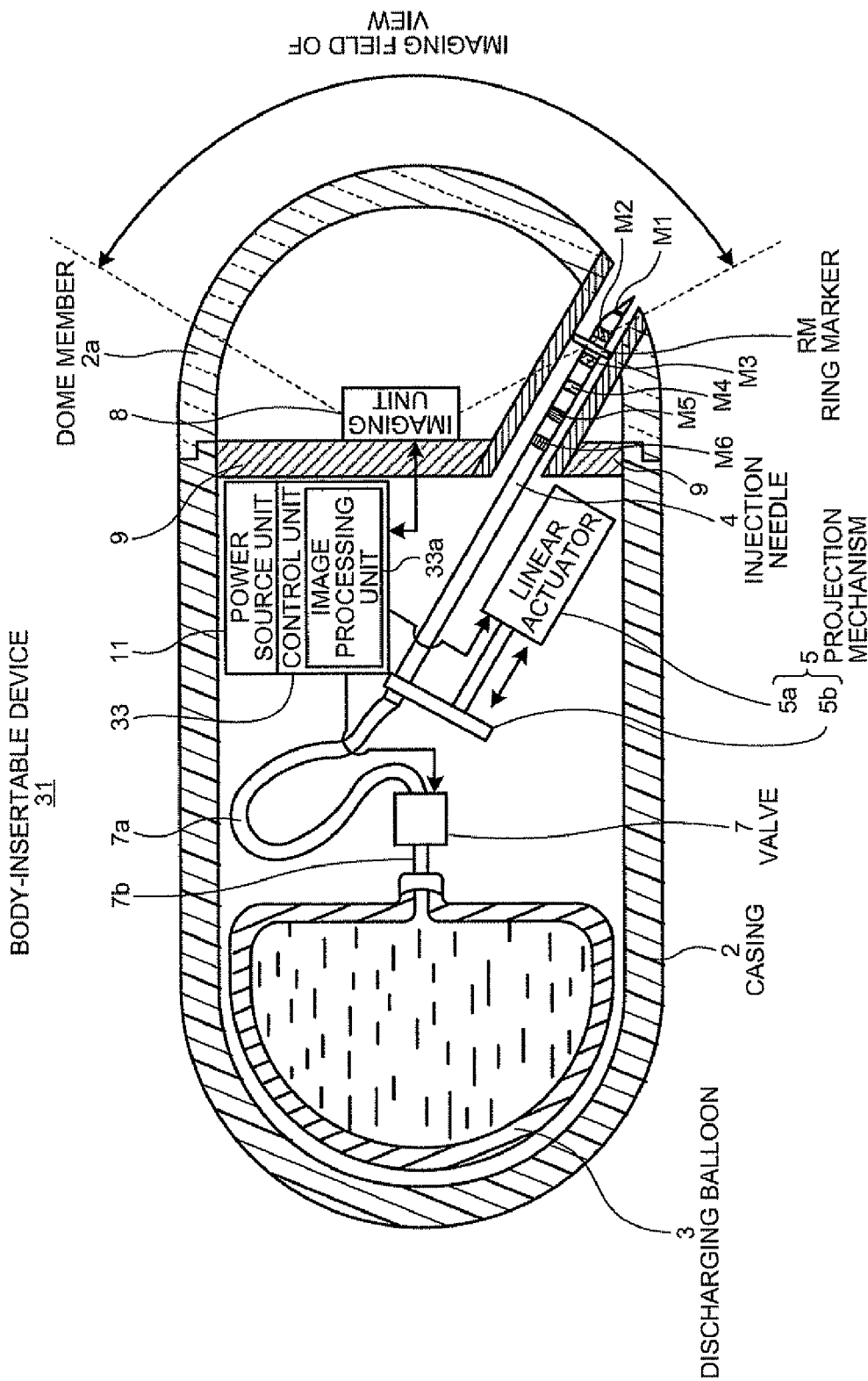
FIG. 15 is a sectional schematic diagram schematically illustrating a configuring example of a body-insertable device according to the third embodiment of the present invention.

FIG. 15 is a sectional schematic diagram schematically illustrating a configuring example of a body-insertable device according to the third embodiment of the present invention. As illustrated in FIG. 15, a body-insertable device 31 has a control unit 33 in place of the control unit 10 of the body-insertable device 1 according to the first embodiment, and a circular ring marker RM provided at the tip of the injection needle 4. The injection needle 4 has the color markers M5 and M6 formed at predetermined intervals at its base end as compared to the color marker M4. The color markers M1 to M6 are formed so as to have a predetermined width in the longitudinal direction of the injection needle 4. The colors of the color markers M1 to M6 are easy to be distinguished from the biological tissue surface in the body, and are different from each other. Other configuration is the same as that of the first embodiment. The same configuring parts are indicated by similar reference numerals, and the description is omitted.

The ring marker RM is a circular marker used for calculating the puncture angle θ of the injection needle 4 with respect to the biological tissue surface. Specifically, the ring marker RM is a ring-like member through which the injection needle 4 is inserted into near the center of the circular shape and is slidably provided at the tip of the injection needle 4. The ring marker RM can change its angle with respect to the longitudinal direction of the injection needle 4. When the injection needle 4 punctures the biological tissue, the ring marker RM is pressed onto the biological tissue surface to change its angle formed with the longitudinal direction of the injection needle 4 corresponding to the biological tissue surface. The detail of the ring marker RM will be described later.

In substantially the same manner as that of the control unit 10 of the body-insertable device 1 according to the first embodiment, the control unit 33 functions to control driving of the linear actuator 5a, the imaging unit 8, and the valve 7. Specifically, the control unit 33 controls driving of the valve 7 to start or stop the discharging operation of the liquid medicine by the discharging balloon 3. The control unit 33 controls driving of the linear actuator 5a and the imaging unit 8 at substantially the same timing as that of the control unit 10. The control unit 33 obtains an image showing the position relation between the biological tissue surface in the body and the injection needle 4 each time the injection needle 4 is moved by the predetermined unit amount, e.g., an image including the injection needle 4 exposed on the projection trajectory and the ring marker RM in the detection region A1.

The control unit 33 has an image processing unit 33a in place of the image processing unit 10a of the control unit 10. In substantially the same manner as that of the image processing unit 10a, the image processing unit 33a detects the color of the color marker at the distal end from the color markers in the detection region A1 according to the image imaged by the imaging unit 8. When the injection needle 4 punctures the biological tissue in the body, the image processing unit 33a detects the ring marker RM according to the image. The image processing unit 33a calculates the puncture angle θ of the injection needle 4 with respect to the biological tissue surface according to the degree of deformation of the detected ring marker RM (that is, the degree of deformation from the original circular shape to an elliptical shape).

According to the color of the color marker at the distal end and the puncture angle θ of the injection needle 4 obtained by the image processing unit 33a, the control unit 33 controls driving of the linear actuator 5a to control the amount of projection of the injection needle 4. The control unit 33 controls the puncture depth of the injection needle 4 puncturing the biological tissue to the desired puncture depth. In substantially the same manner as that of the control unit 23 of the body-insertable device 21 according to the second embodiment, the control unit 33 knows the position relation between the injection needle 4 and the biological tissue surface according to the color of the color marker at the distal end. The control unit 33 then controls the amount of projection of the injection needle 4 corresponding to the puncture angle θ with respect to the biological tissue surface. The control unit 33 controls the amount of projection of the injection needle 4 according to the position relation between the biological tissue surface and the injection needle 4 and the puncture angle θ of the injection needle 4. The control unit 33 can reliably control the puncture depth of the injection needle 4 to the desired puncture depth.

When the color marker M1 is the color marker at the distal end, the control unit 33 knows that the injection needle 4 does not puncture the biological tissue surface. The control unit 33 controls driving of the linear actuator 5a as in the control unit 10 without depending on the penetrating angle of the injection needle 4 with respect to the biological tissue surface. The control unit 33 then moves the injection needle 4 in the projecting direction until the position relation between the injection needle 4 and the biological tissue surface becomes the position relation in puncturing state. Until the injection needle 4 punctures the biological tissue, the image processing unit 33a needs not calculate the puncture angle of the injection needle 4.

Figure 16:
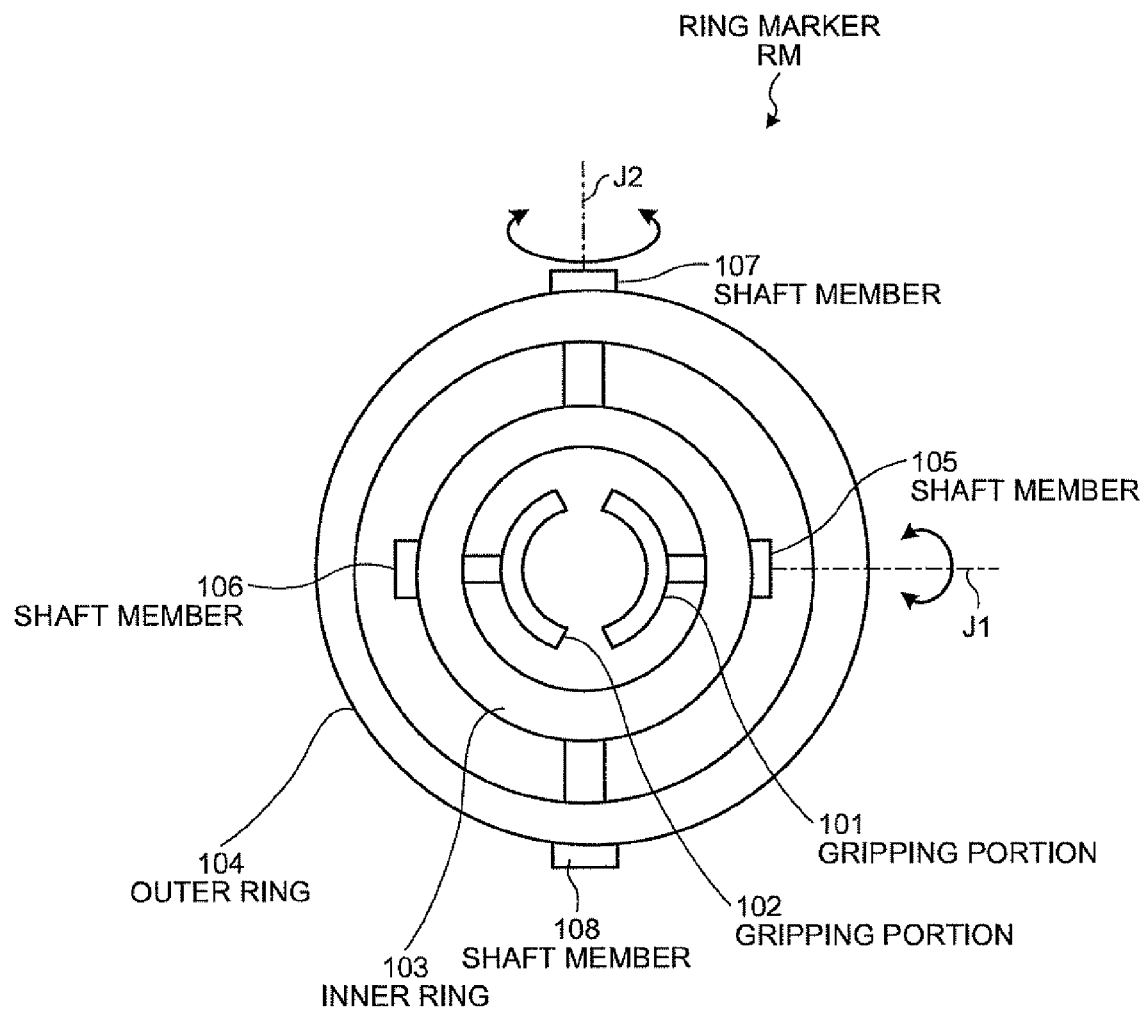
FIG. 16 is a schematic diagram schematically illustrating a configuring example of a ring marker.

The configuration of the ring marker RM will be described in detail. FIG. 16 is a schematic diagram schematically illustrating a configuring example of the ring marker RM. As illustrated in FIG. 16, the ring marker RM has a pair of gripping portions 101 and 102 which slidably grip the injection needle 4, an inner ring 103 rotatable with respect to the pair of gripping portions 101 and 102 about a rotating axis J1, and an outer ring 104 rotatable with respect to the inner ring 103 about a rotating axis J2 vertical to the rotating axis J1.

The pair of gripping portions 101 and 102 are arcuate members and slidably grip the injection needle 4 by sandwiching it. Specifically, the gripping portions 101 and 102 are arranged such that they are opposite to each other in a throughhole of the inner ring 103 which is a circular ring-like member, and are rotatably attached to the inner ring 103 by shaft members 105 and 106 aligned on a straight line. The gripping portions 101 and 102 can slidably grip the injection needle 4 in the throughhole of the inner ring 103, preferably, around the center of the circular shape formed by the inner ring 103. The gripping portions 101 and 102 are rotatable with respect to the inner ring 103 about the rotating axis J1 formed by the shaft members 105 and 106. The inner ring 103 is rotatable with respect to the injection needle 4 gripped by the gripping portions 101 and 102 about the rotating axis J1.

The outer ring 104 forms an outer shape of the ring marker RM. Specifically, the outer ring 104 is a circular ring-like member which forms a throughhole having a diameter larger than that of the inner ring 103. The outer ring 104 is rotatably attached to the inner ring 103 arranged in the throughhole by shaft members 107 and 108 aligned on a straight line. The outer ring 104 is vertical to the rotating axis J1 and is rotatable with respect to the inner ring 103 about the rotating axis J2 formed by the shaft members 107 and 108. The outer ring 104 can change its angle with respect to the longitudinal direction of the injection needle 4 gripped by the gripping portions 101 and 102.

It is desirable that the inner ring 103 and the outer ring 104 be arranged such that the centers of the circular shapes are matched with each other. It is desirable that the inner ring 103 and the outer ring 104 be arranged such that the points of intersection of the rotating axes J1 and J2 are located at the centers of the circular shapes, respectively.

Figure 17:
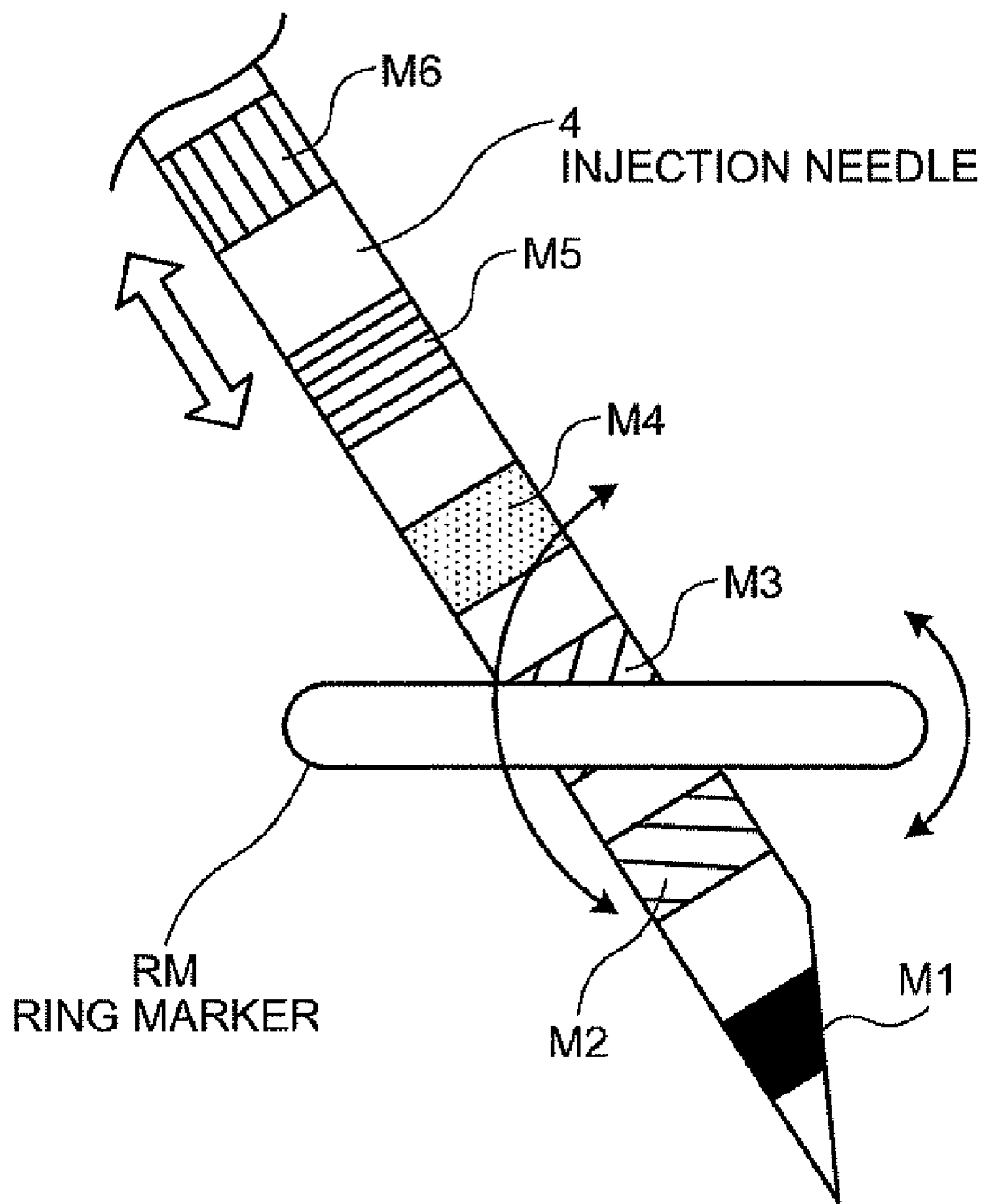
FIG. 17 is a schematic diagram illustrating a tip of the injection needle provided with the ring marker.

As illustrated in FIG. 17, the ring marker RM having such a configuration is slidably attached to the tip of the injection needle 4 and is rotated so as to change its angle with respect to the longitudinal direction of the injection needle 4. When the injection needle 4 punctures the biological tissue in the body, the ring marker RM is pressed onto the biological tissue surface. The ring marker RM then changes its angle with respect to the longitudinal direction of the injection needle 4 corresponding to the biological tissue surface. When the injection needle 4 punctures the biological tissue, a plane including the circular shape of the ring marker RM (specifically, the outer ring 104) is tilted with respect to the axis of the injection needle 4 in the longitudinal direction corresponding to the biological tissue surface. The angle formed between the plane including the circular shape of the ring marker RM and the axis of the injection needle 4 in the longitudinal direction is the puncture angle θ of the injection needle 4 with respect to the biological tissue surface.

Figure 18:
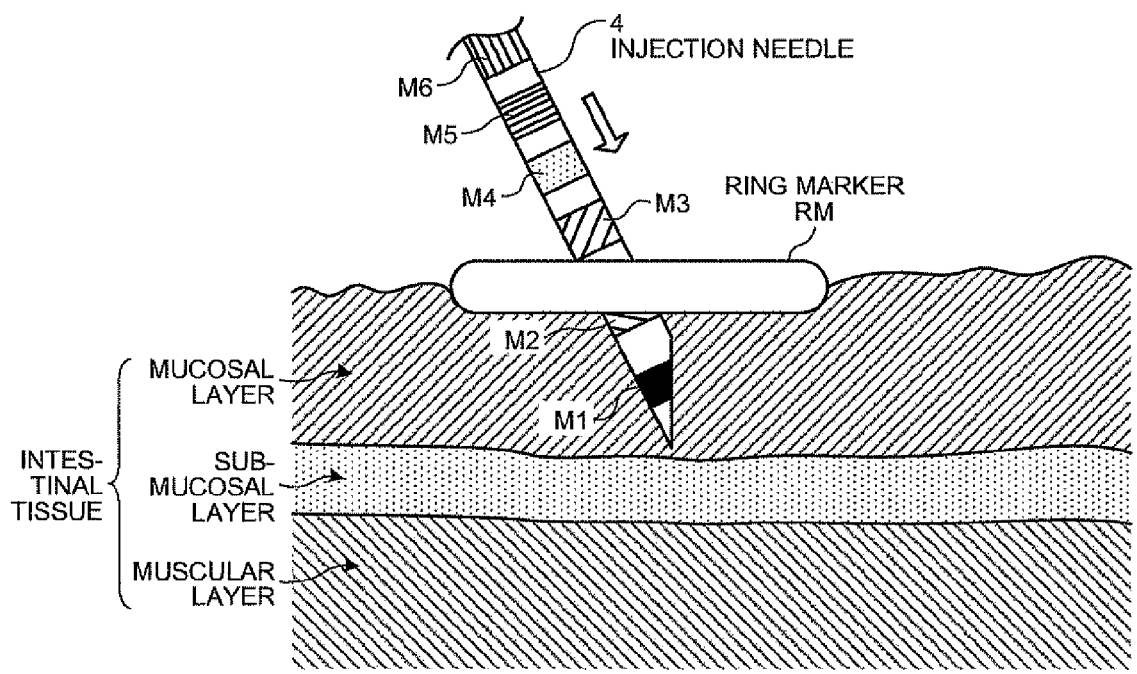
FIG. 18 is a schematic diagram illustrating the state in which the ring marker is pressed onto the biological tissue surface and the injection needle punctures the biological tissue.

The operation of the body-insertable device 31 which controls the puncture depth of the injection needle 4 which punctures the desired part in the body to the desired puncture depth will be specifically described. FIG. 18 is a schematic diagram illustrating the state in which the ring marker RM is pressed onto the biological tissue surface and the injection needle 4 punctures the biological tissue. The operation of the control unit 33 which controls the puncture depth of the injection needle 4 to the desired puncture depth at high accuracy will be described below by illustrating the case in which the liquid medicine is injected into the submucosal layer of the small intestine which is an example of the desired part in the body.

In step S103 of the processing procedure in steps S101 to S107 (see FIG. 3), the body-insertable device 31 detects the position relation between the injection needle 4 and the biological tissue surface and the puncture angle of the injection needle 4 with respect to the biological tissue surface according to the image which images the injection needle 4 on the projection trajectory and the ring marker RM. In step S105, the body-insertable device 31 controls the puncture depth of the injection needle 4 from the biological tissue surface to the desired puncture depth according to the position relation between the injection needle 4 and the biological tissue surface and the necessary amount of projection of the injection needle 4 changed by the puncture angle of the injection needle 4. The remaining processing procedure of the body-insertable device 31 (steps S101, S102, S104, S106, and S107) is the same as that of the first embodiment.

The body-insertable device 31 introduced into the body reaches the desired part, e.g., the small intestine, in the body. The control unit 33 repeatedly controls driving of the linear actuator 5a and the imaging unit 8 in substantially the same manner as that of the first embodiment until the injection needle 4 punctures the intestinal tissue (that is, the position relation in puncturing state). As illustrated in FIG. 18, the injection needle 4 presses the ring marker RM at its tip onto the intestinal tissue surface, and is slid between the griping portions 101 and 102 to puncture the intestinal tissue. The control unit 33 controls driving of the imaging unit 8. The control unit 33 obtains an image including the ring marker RM pressed onto the intestinal tissue surface and the injection needle 4 puncturing the intestinal tissue. The imaging unit 8 can easily image the ring marker RM tilted corresponding to the intestinal tissue surface punctured by the injection needle 4.

The image processing unit 33a detects the color of the color marker at the distal end from the color markers included in the detection region A1 according to the image imaged by the imaging unit 8. The image processing unit 33a detects a figure of the ring marker RM imaged in the image and detects the degree of deformation of the detected figure of the ring marker RM. The image processing unit 33a calculates the puncture angle θ of the injection needle 4 with respect to the intestinal tissue surface according to the degree of deformation of the imaged ring marker RM (deformation from the original circular shape to an elliptical shape).

Figure 19:
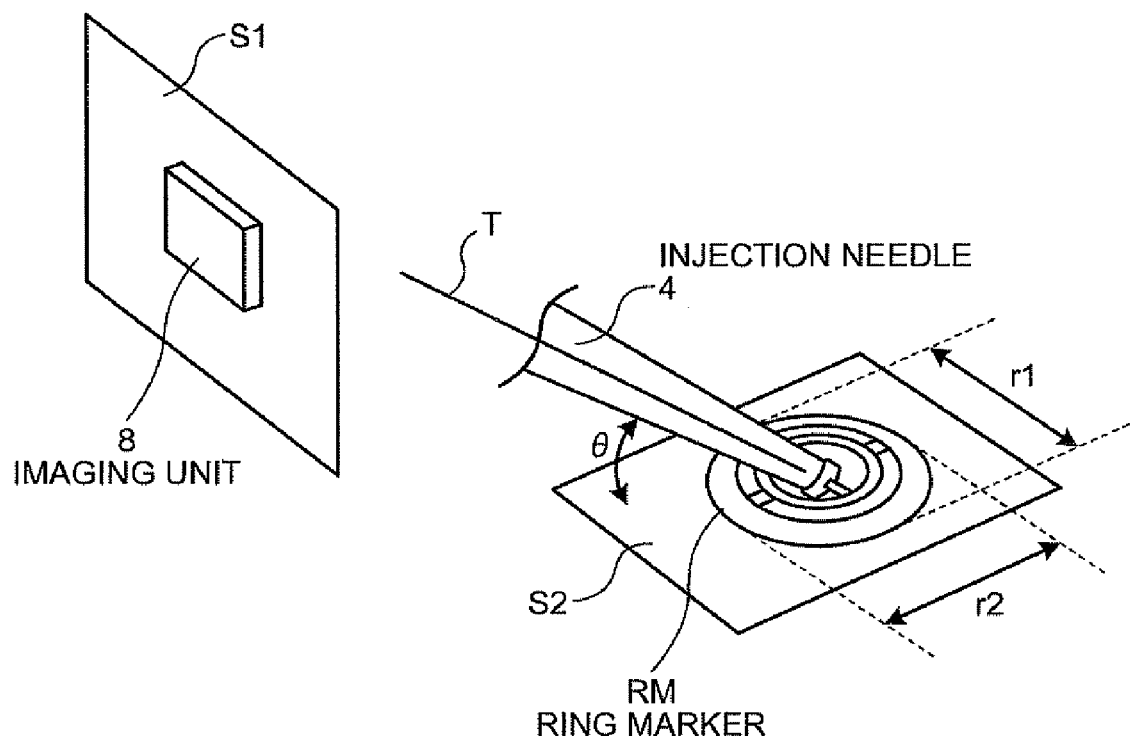
FIG. 19 is a schematic diagram for explaining processing of the image processing unit which calculates the puncture angle of the injection needle with respect to the biological tissue surface pressed by the ring marker.

Processing of the image processing unit 33a which calculates the puncture angle θ of the injection needle 4 with respect to the biological tissue surface will be described here. FIG. 19 is a schematic diagram for explaining the processing of the image processing unit 33a which calculates the puncture angle θ of the injection needle 4 which punctures the desired part in the body.

As described above, the imaging unit 8 is fixed in a predetermined direction by the supporting member 9 and is in a predetermined position relation between it and a axis T of the injection needle 4 in the longitudinal direction. In FIG. 19, a plane S1 including the light receiving surface of the imaging unit 8 is fixed to the axis T, and the angle formed between the plane S1 and the axis T is constant. As described above, the ring marker RM is rotated so as to change its angle with respect to the longitudinal direction of the injection needle 4. A plane S2 including the circular shape of the ring marker RM (specifically, the circular shape of the outer ring 104) can change its angle with respect to the axis T of the injection needle 4. Specifically, when the ring marker RM is pressed onto the biological tissue surface, the plane S2 is tilted with respect to the axis T of the injection needle 4 corresponding to the biological tissue surface. A minimum value of the angle formed between the plane S2 and the axis T is the puncture angle θ of the injection needle 4 with respect to the biological tissue surface.

When the angle formed between the plane S2 and the axis T is 90°, the ring marker RM indicates a substantially circular shape to the imaging unit 8. When tilted corresponding to the biological tissue surface as described above, the ring marker RM indicates a perspective figure of the circular shape, that is, an elliptical shape deformed from the circular shape, to the imaging unit 8. The degree of deformation of the ring marker RM from the circular shape to the elliptical shape depends on the angle formed between the plane S2 and the axis T changed corresponding to the biological tissue surface (that is, the tilt of the axis T with respect to the plane S2). When the angle formed between the plane S2 and the axis T is 90°, the imaging unit 8 images an image of the ring marker RM in substantially circular shape. When the plane S2 is tilted corresponding to the biological tissue surface, the imaging unit 8 images an image of the ring marker RM deformed from the circular shape to the elliptical shape corresponding to the angle formed between the plane S2 and the axis T.

The image processing unit 33a detects the degree of deformation of the ring marker RM from the circular shape to the elliptical shape according to the image imaged by the imaging unit 8. Specifically, the image processing unit 33a calculates an outer diameter r1 in the same direction as that of the rotating axis J1 and an outer diameter r2 in the same direction as that of the rotating axis J2 of the figure of the ring marker RM detected according to the image. The image processing unit 33a detects the degree of deformation of the ring marker RM from the circular shape to the elliptical shape imaged in the image according to the change of the outer diameters r1 and r2 as compared to the outer diameter (a diameter) originally formed by the ring marker RM. The image processing unit 33a detects the position relation between the plane S1 including the light receiving surface of the imaging unit 8 and the plane S2 including the circular shape of the ring marker RM according to the degree of deformation of the ring marker RM. The image processing unit 33a then calculates the angle formed between the plane S1 and the plane S2. The control unit 33 previously stores the fixed position relation between the axis T of the injection needle 4 and the plane S1 and knows the angle formed between the axis T and the plane S1. The image processing unit 33a calculates the angle formed between the axis T and the plane S2, that is, the puncture angle θ of the injection needle 4 with respect to the biological tissue surface according to the angle formed between the planes S1 and S2 and the angle formed between the axis T and the plane S1.

According to the puncture angle θ calculated by the image processing unit 33a and the color of the color marker at the distal end, the control unit 33 controls driving of the linear actuator 5a to control the amount of projection of the injection needle 4. The control unit 33 controls the puncture depth of the injection needle 4 from the biological tissue surface to the desired puncture depth. In substantially the same manner as that of the control unit 23 of the body-insertable device 21 according to the second embodiment, the control unit 33 switches, as the color of the color marker at the distal end which is judged to be the desired puncture depth, between the color markers M2 to M6 corresponding to the puncture angle θ calculated by the image processing unit 33a, thereby increasing and decreasing the amount of projection of the injection needle 4. The amount of projection of the injection needle 4 is controlled corresponding to the puncture angle θ. The control unit 33 can reliably control the puncture depth of the injection needle 4 from the biological tissue surface to the desired puncture depth, e.g., the puncture depth corresponding to the submucosal layer of the intestinal tissue, even if the puncture angle θ of the injection needle 4 is changed according to the puncture position of the biological tissue as illustrated in the uneven surface of the intestinal tissue.

As described above, according to the third embodiment of the present invention, the body-insertable device 31 has the above configuration. The puncture position of the injection needle into the biological tissue can be easily detected by the ring marker tilted corresponding to the biological tissue surface. The biological tissue surface tilted in the longitudinal direction of the injection needle can be easily detected. The body-insertable device which can have substantially the same operation and effect as those of the second embodiment and easily calculate the puncture angle of the injection needle with respect to the biological tissue surface can be realized.

When the injection needle punctures the biological tissue, the biological tissue surface is pressed by the ring marker. Sliding of the injection needle on the biological tissue surface can be suppressed. Shifting of the puncture position of the injection needle can be suppressed. The injection needle can easily puncture the desired biological tissue.

A fourth embodiment of the present invention 4 will be described. In the first embodiment, the puncture depth of the injection needle into the biological tissue is controlled according to the color of the color marker formed on the injection needle. In the fourth embodiment, the liquid medicine is discharged from the tip of the injection needle each time the injection needle is projected by the predetermined unit amount to judge whether or not the liquid medicine is discharged onto the biological tissue surface, and according to the judged result, the puncture depth of the injection needle into the biological tissue is controlled.

Figure 20:
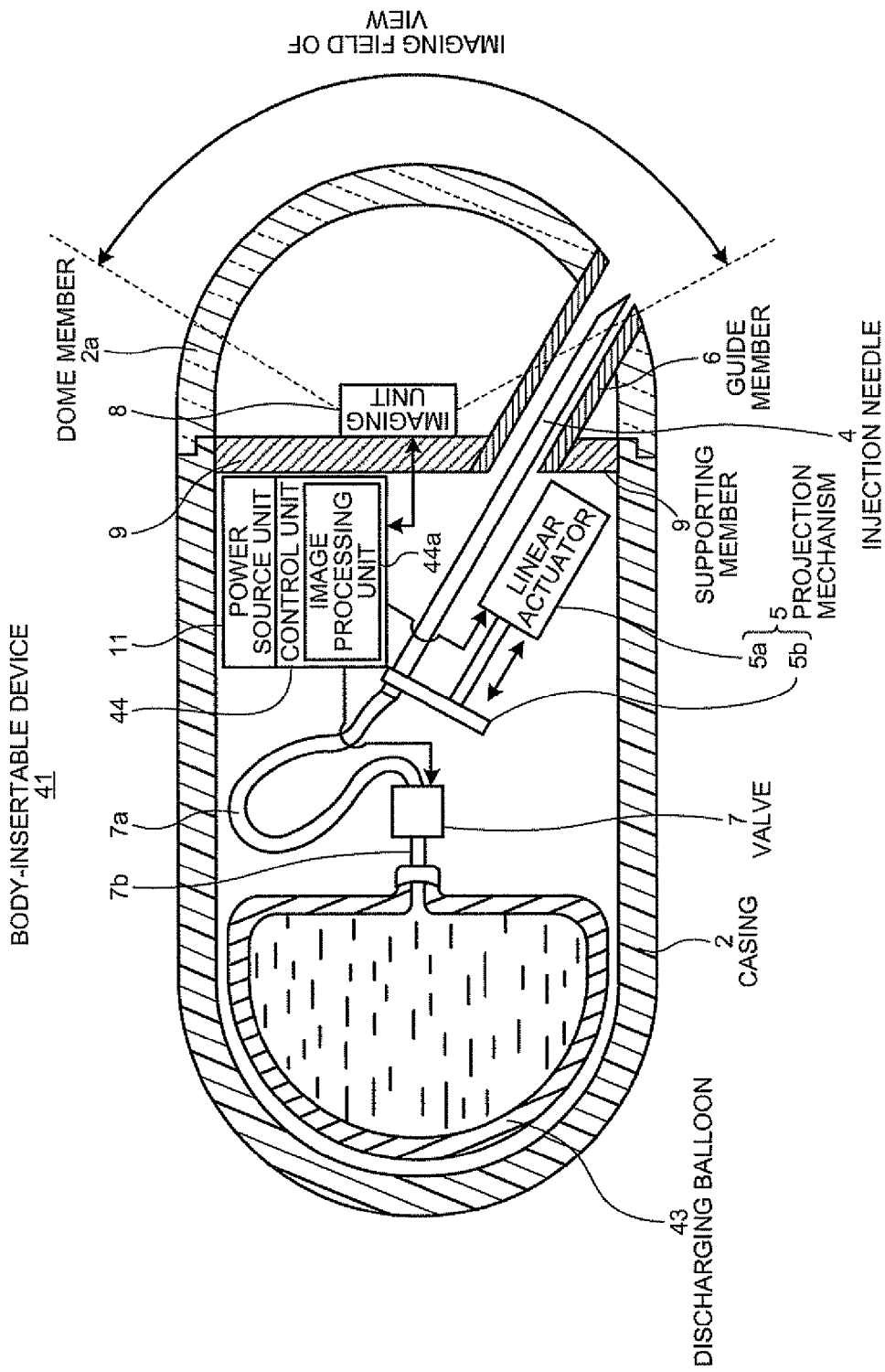
FIG. 20 is a sectional schematic diagram schematically illustrating a configuring example of a body-insertable device according to the fourth embodiment of the present invention.

FIG. 20 is a sectional schematic diagram schematically illustrating a configuring example of a body-insertable device according to the fourth embodiment of the present invention. As illustrated in FIG. 20, a body-insertable device 41 has a discharging balloon 43 in place of the discharging balloon 3 of the body-insertable device 1 according to the first embodiment, and a control unit 44 in place of the control unit 10. The color markers are not provided on the injection needle 4. Other configuration is the same as that of the first embodiment. The same configuring parts are indicated by similar reference numerals, and the description is omitted.

The discharging balloon 43 forms a storage chamber which stores a liquid medicine colored in a color which is easy to be distinguished from the color of the biological tissue surface (hereinafter, called a colored liquid medicine). The discharging balloon 43 functions as discharging means which discharges the colored liquid medicine to the duct line of the injection needle 4 through the valve 7 and the tubes 7a and 7b. Specifically, the discharging balloon 43 is realized by an elastic member such as rubber, and in substantially the same manner as that of the discharging balloon 3 of the body-insertable device 1 according to the first embodiment, functions to discharge the colored liquid medicine by its own contracting force. The discharging balloon 43 communicates with the valve 7 through the tube 7b. When the valve 7 is open-driven, the discharging balloon 43 is contracted by its own contracting force and applies a pressure to the colored liquid medicine to perform the discharging operation of the colored liquid medicine. The colored liquid medicine discharged by the discharging balloon 43 sequentially circulates through the tube 7b, the valve 7, and the tube 7a to reach the duct line of the injection needle 4. The colored liquid medicine circulates through the duct line of the injection needle 4 to flow out from the tip of the injection needle 4. When the valve 7 is close-driven, the discharging balloon 43 stops the contraction to stop the discharging operation of the colored liquid medicine.

As described above, the color of the colored liquid medicine is desirably the color which is easy to be distinguished from the color of the biological tissue surface in the body, e.g., green, indigo blue, blue, or purple. The colored liquid medicine forms contrast which clarifies the boundary between it and the biological tissue surface in the body in an image imaged by the imaging unit 8.

In substantially the same manner as the control unit 10 of the body-insertable device 1 according to the first embodiment, the control unit 44 has a function of controlling driving of the linear actuator 5a, the valve 7, and the imaging unit 8. Specifically, the control unit 44 controls driving of the linear actuator 5a to control the amount of projection of the injection needle 4. The control unit 44 controls driving of the imaging unit 8 to obtain an image showing the position relation between the injection needle 4 and the biological tissue surface. The control unit 44 controls driving of the valve 7 to start or stop the discharging operation of the colored liquid medicine by the discharging balloon 43.

The control unit 44 controls driving of the linear actuator 5a and the imaging unit 8 at substantially the same timing as that of the control unit 10, and controls driving of the valve 7. The control unit 44 controls driving of the linear actuator 5a, and then moves the injection needle 4 by the predetermined unit amount in the projecting direction or the housing direction. At the same time, the control unit 44 repeatedly controls open- and close-driving of the valve 7 each time the injection needle 4 is moved by the predetermined unit amount, and then discharges a very small amount of the colored liquid medicine from the tip of the injection needle 4. The control unit 44 controls driving of the imaging unit 8 each time the very small amount of the colored liquid medicine is discharged from the tip of the injection needle 4 to obtain the image imaged by the imaging unit 8. The control unit 44 knows the position relation between the injection needle 4 and the biological tissue surface according to the image obtained from the imaging unit 8. According to the position relation, the control unit 44 controls driving of the linear actuator 5a to control the amount of projection of the injection needle 4. The control unit 44 then controls the puncture depth of the injection needle 4 from the biological tissue surface to the desired puncture depth.

The control unit 44 has an image processing unit 44a in place of the image processing unit 10a of the control unit 10. The image processing unit 44a detects spread of the colored liquid medicine on the biological tissue surface according to the image imaged by the imaging unit 8. Here, the position relation between the injection needle 4 and the biological tissue surface is the position relation in non-puncturing state (that is, the duct line opening at the tip of the injection needle 4 is exposed on the biological tissue surface). The colored liquid medicine discharged from the tip of the injection needle 4 flows out onto the biological tissue surface, and is then spread. The imaging unit 8 images, as the image showing the position relation between the injection needle 4 and the biological tissue surface, an image including the colored liquid medicine spread onto the biological tissue surface.

The image processing unit 44a calculates the area occupied by the colored liquid medicine on the biological tissue surface according to the present image imaged by the imaging unit 8. The image processing unit 44a compares the area of the colored liquid medicine calculated according to a previous image and the present area. The image processing unit 44a detects spread of the colored liquid medicine on the biological tissue surface according to the result of the comparison processing according to the images. The occupation area of the colored liquid medicine according to the present image (the present occupation area) is larger than the occupation area of the colored liquid medicine according to the previous image (the previous occupation area). Then, the image processing unit 44a detects spread of the colored liquid medicine on the biological tissue surface. The present occupation area is smaller than the previous occupation area. Then, the image processing unit 44a detects that there is no spread of the colored liquid medicine on the biological tissue surface.

According to the detected result by the image processing unit 44a, the control unit 44 controls driving of the linear actuator 5a to control the amount of projection of the injection needle 4. The control unit 44 controls the puncture depth of the injection needle 4 from the biological tissue surface to the desired puncture depth. The image processing unit 44a detects spread of the colored liquid medicine on the biological tissue surface. Then, the control unit 44 judges that the position relation between the biological tissue surface and the injection needle 4 is the position relation in non-puncturing state. The control unit 44 controls driving of the linear actuator 5a to project the injection needle 4. The control unit 44 repeatedly controls driving of the valve 7, the imaging unit 8, and the linear actuator 5a. On the other hand, the image processing unit 44a detects that there is no spread of the colored liquid medicine. Then, the control unit 44 judges that the position relation between the biological tissue surface and the injection needle 4 is the position relation in puncturing state and that the puncture depth of the injection needle 4 from the biological tissue surface is the desired puncture depth. The control unit 44 controls driving of the valve 7 to start the discharging operation of the colored liquid medicine by the discharging balloon 43. The control unit 44 injects the predetermined amount of the liquid medicine into the layer at the desired puncture depth in the biological tissue.

As described above, the colored liquid medicine discharged from the tip of the injection needle 4 is colored in the color which is easy to be distinguished from the biological tissue surface. The image processing unit 44a can easily detect the colored liquid medicine spread on the biological tissue surface according to the image imaged by the imaging unit 8.

Figure 21:
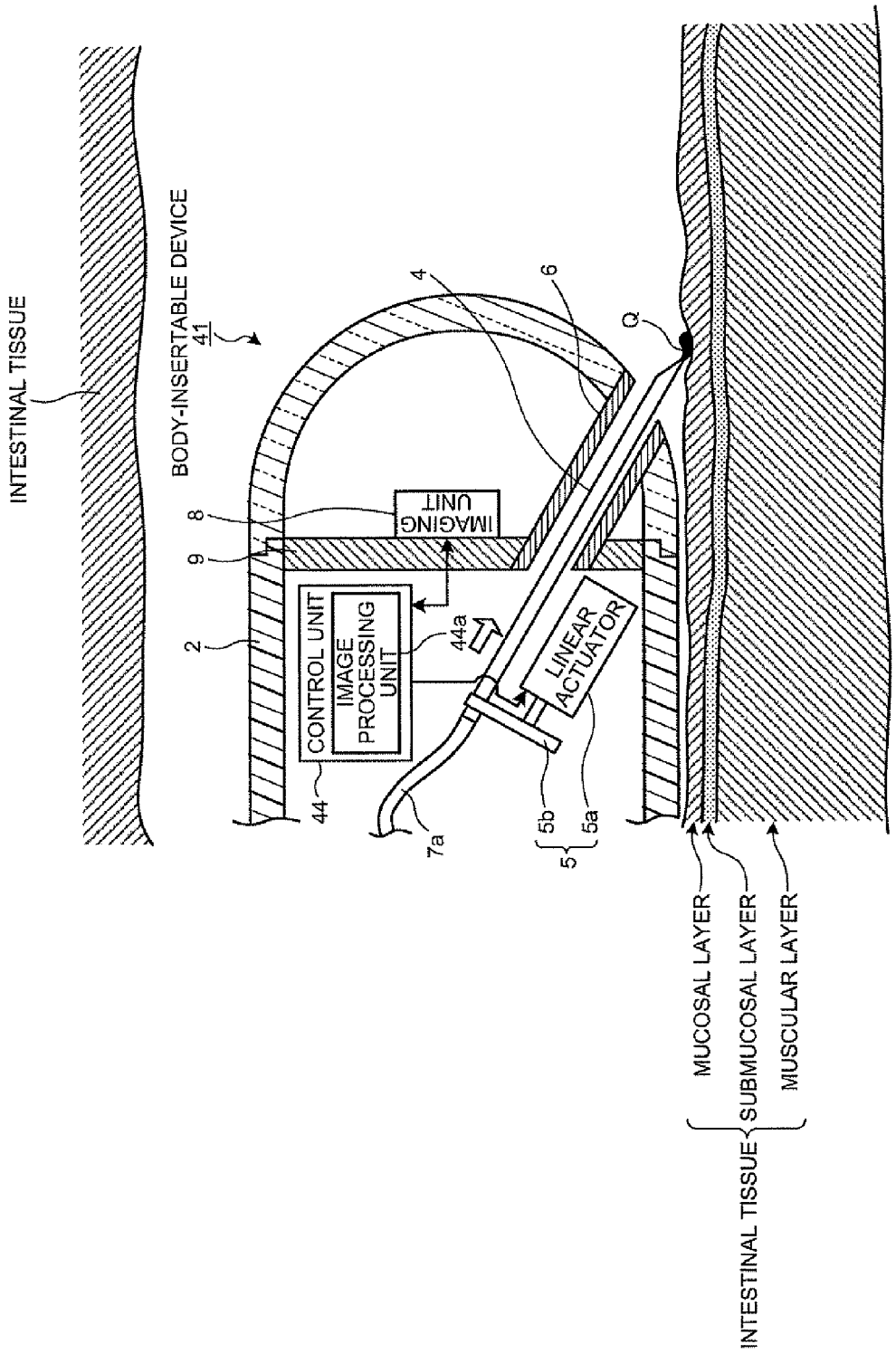
FIG. 21 is a schematic diagram for explaining the operation of a control unit which controls the puncture depth of the injection needle according to the presence or absence of spread of a colored liquid medicine on the biological tissue surface.

The operation of the body-insertable device 41 which controls the puncture depth of the injection needle 4 which punctures the desired part in the body will be specifically described. FIG. 21 is a schematic diagram for explaining the operation of the control unit 44 which controls the puncture depth of the injection needle 4 according to the presence or absence of spread of the colored liquid medicine on the biological tissue surface. The operation of the control unit 44 which controls the puncture depth of the injection needle 4 to the desired puncture depth will be described below with reference to FIG. 21 by illustrating the case in which the liquid medicine is injected into the submucosal layer of the small intestine which is an example of the desired part in the body.

In step S103 of the processing procedure in steps S101 to S107 (see FIG. 3), according to a series of images which image the colored liquid medicine discharged onto the biological tissue surface via the injection needle 4, the body-insertable device 41 detects the position relation between the injection needle 4 and the biological tissue surface. In step S105, the body-insertable device 41 controls the puncture depth of the injection needle 4 from the biological tissue surface to the desired puncture depth according to the position relation between the injection needle 4 and the biological tissue surface detected by comparison processing of the series of images imaging the colored liquid medicine. The remaining processing procedure of the body-insertable device 41 (steps S101, S102, S104, S106, and S107) is the same as that of the first embodiment.

Figure 22:
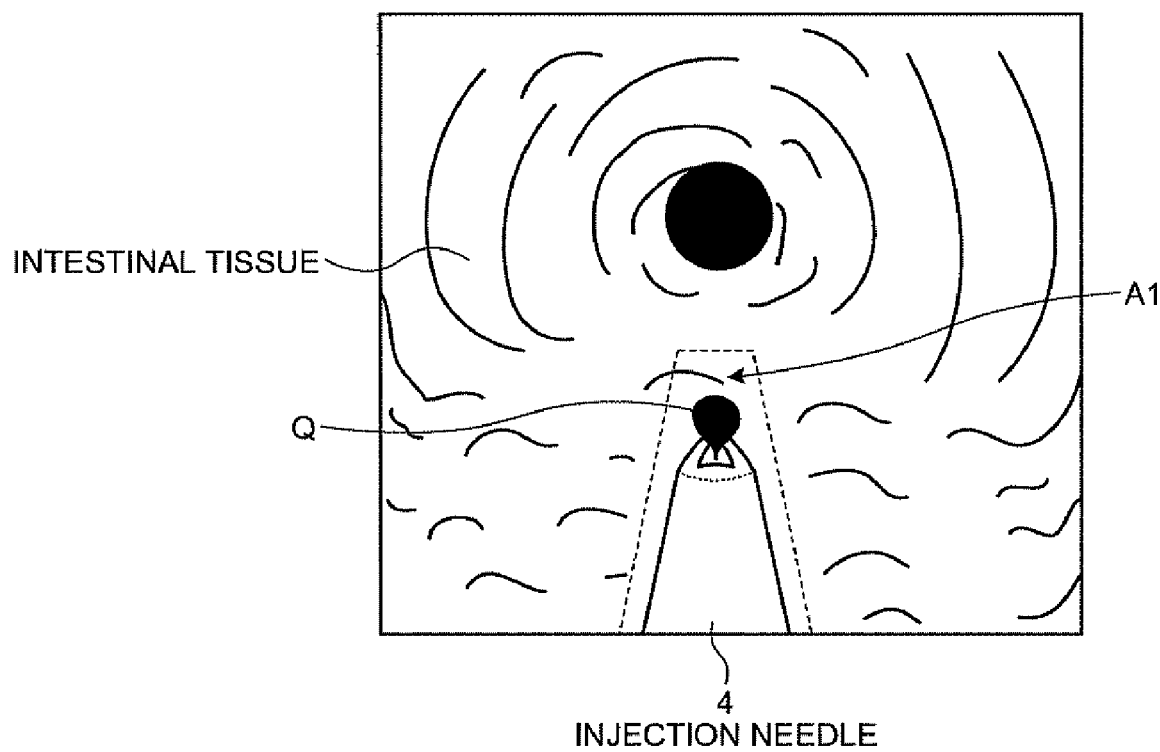
FIG. 22 is a schematic diagram illustrating a specific example of an image including the injection needle in non-puncturing state and a liquid sump of the colored liquid medicine.

The body-insertable device 41 introduced into the body reaches the desired part in the body, e.g., the small intestine. The control unit 44 controls driving of the linear actuator 5a to project the injection needle 4 from the casing 2 by the predetermined unit amount. At the same time, the control unit 44 controls open- and close-driving of the valve 7, and then discharges a very small amount of the colored liquid medicine from the tip of the injection needle 4 projected by the predetermined unit amount. As illustrated in FIG. 21, the colored liquid medicine discharged from the tip of the injection needle 4 flows out onto the intestinal tissue surface to form a liquid sump Q. The control unit 44 controls driving of the imaging unit 8 following the driving control of the valve 7. The control unit 44 obtains an image showing the position relation between the injection needle 4 and the intestinal tissue surface. As illustrated in FIG. 22, the imaging unit 8 images an image including the liquid sump Q of the colored liquid medicine in the detection region A1.

The image processing unit 44a detects the presence or absence of spread of the colored liquid medicine on the intestinal tissue surface according to the image imaged by the imaging unit 8. Specifically, the image processing unit 44a detects the present liquid sump Q from the detection region A1 of the image illustrated in FIG. 22. The occupation area of the present liquid sump Q is larger than the previous liquid sump Q included in the detection area A1 of the previous image. Then, the image processing unit 44a detects spread of the colored liquid medicine on the intestinal tissue surface. The image illustrated in FIG. 22 is an image imaged first in the series of operation of the control unit 44 which controls the amount of projection of the injection needle 4. Then, the image processing unit 44a detects the liquid sump Q from the detection region A1 of the image to detect spread of the colored liquid medicine on the intestinal tissue surface.

The image processing unit 44a detects spread of the colored liquid medicine on the intestinal tissue surface. The control unit 44 judges that the position relation between the intestinal tissue surface and the injection needle 4 is the position relation in non-puncturing state. The control unit 44 controls driving of the linear actuator 5a to project the injection needle 4, and then punctures the intestinal tissue via the injection needle 4. Until the control unit 44 controls the puncture depth of the injection needle 4 from the intestinal tissue surface to the desired puncture depth, it repeatedly controls driving of the valve 7, the imaging unit 8, and the linear actuator 5a.

Figure 23:
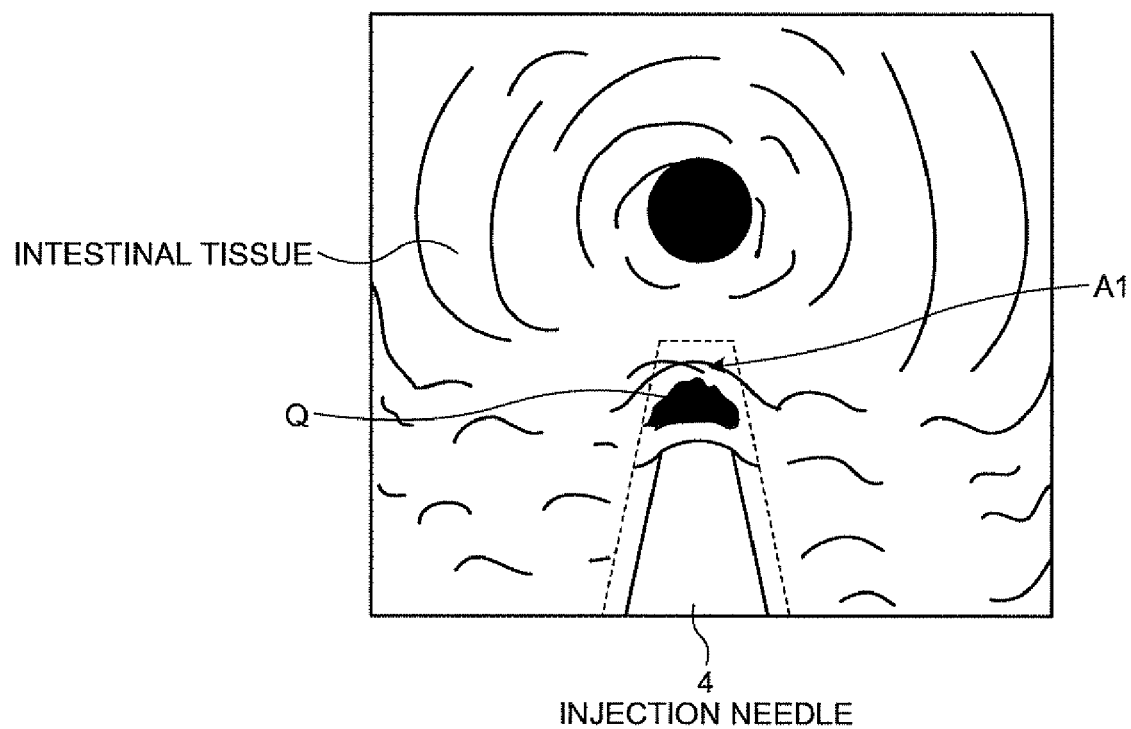
FIG. 23 is a schematic diagram illustrating a specific example of an image including the injection needle which punctures the intestinal tissue to the desired puncture depth and the liquid sump of the colored liquid medicine.

The control unit 44 controls driving of the linear actuator 5a to project the injection needle 4 toward the submucosal layer. The control unit 44 controls open- and close-driving of the valve 7 to discharge the colored liquid medicine from the tip of the injection needle 4. The control unit 44 controls driving of the imaging unit 8 to obtain an image imaged by the imaging unit 8. As illustrated in FIG. 23, the imaging unit 8 images an image of the injection needle 4 puncturing the intestinal tissue and the liquid sump Q.

The image illustrated in FIG. 23 is imaged. The image processing unit 44a detects the present liquid sump Q from the detection region A1 of the image. The image processing unit 44a compares the occupation area of the previous liquid sump Q included in the detection region A1 of the previous image with the occupation area of the present liquid sump Q. When the occupation area of the present liquid sump Q is smaller than that of the previous liquid sump Q, the image processing unit 44a detects that there is no spread of the colored liquid medicine on the intestinal tissue surface. The injection needle 4 is projected to the puncture depth which locates the duct line opening of the injection needle 4 into the submucosal layer. In this case, the colored liquid medicine does not flow out onto the intestinal tissue surface. The occupation area of the liquid sump Q on the intestinal tissue surface is not increased.

Figure 24:
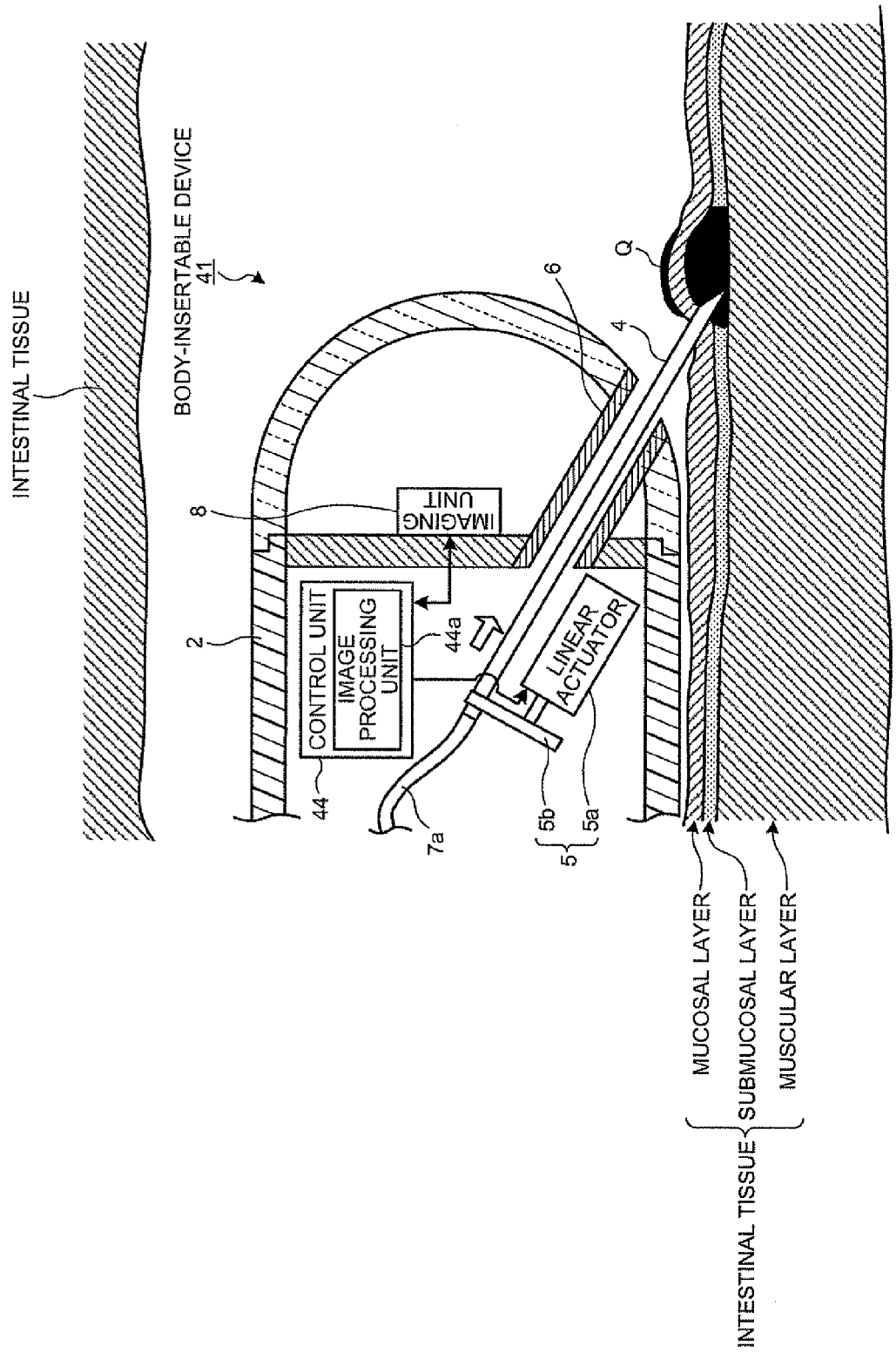
FIG. 24 is a schematic diagram illustrating the state in which the colored liquid medicine is injected into the submucosal layer of the intestinal tissue.

The image processing unit 44a detects that there is no spread of the colored liquid medicine on the intestinal tissue surface. The control unit 44 judges that the position relation between the intestinal tissue surface and the injection needle 4 is the position relation in puncturing state and that the puncture depth of the injection needle 4 from the intestinal tissue surface is the desired puncture depth. As illustrated in FIG. 24, the injection needle 4 which punctures the intestinal tissue locates the duct line opening into the submucosal layer of the intestinal tissue. The control unit 44 controls driving of the valve 7, and can inject a predetermined amount of the colored liquid medicine into the submucosal layer via the injection needle 4.

The control unit 44 detects spread of the liquid sump Q. The control unit 44 reduces the interval which controls the valve from open-driving to close-driving and minimizes the flow rate of the colored liquid medicine flowed out from the tip of the injection needle 4. When spread of the liquid sump Q is substantially absent, the control unit 44 increases the interval which controls the valve from open-driving to close-driving, and then flows out the predetermined amount of the colored liquid medicine from the tip of the injection needle 4. The control unit 44 can control the amount of discharge of the colored liquid medicine according to the degree of spread of the liquid sump Q.

As described above, in the fourth embodiment of the present invention, the body-insertable device 41 has the above configuration. The detecting function which detects the position relation between the biological tissue surface in the body and the injection needle can be realized by a simple configuration. The body-insertable device which can have the same operation and effect as those of the first embodiment and control the puncture depth of the injection needle from the biological tissue surface to the desired puncture depth can be realized.

A fifth embodiment of the present invention 5 will be described. The body-insertable device according to the fifth embodiment has a detecting mechanism which supports the injection needle such that it can be reciprocated in its longitudinal direction and detects the amount of projection of the injection needle necessary for reaching the biological tissue surface in the body and the puncture angle of the injection needle with respect to the biological tissue surface. When the injection needle punctures the biological tissue, the body-insertable device functions to control the amount of projection of the injection needle corresponding to the detected puncture angle of the injection needle and to control the puncture depth of the injection needle from the biological tissue surface to the desired puncture depth.

Figure 25:
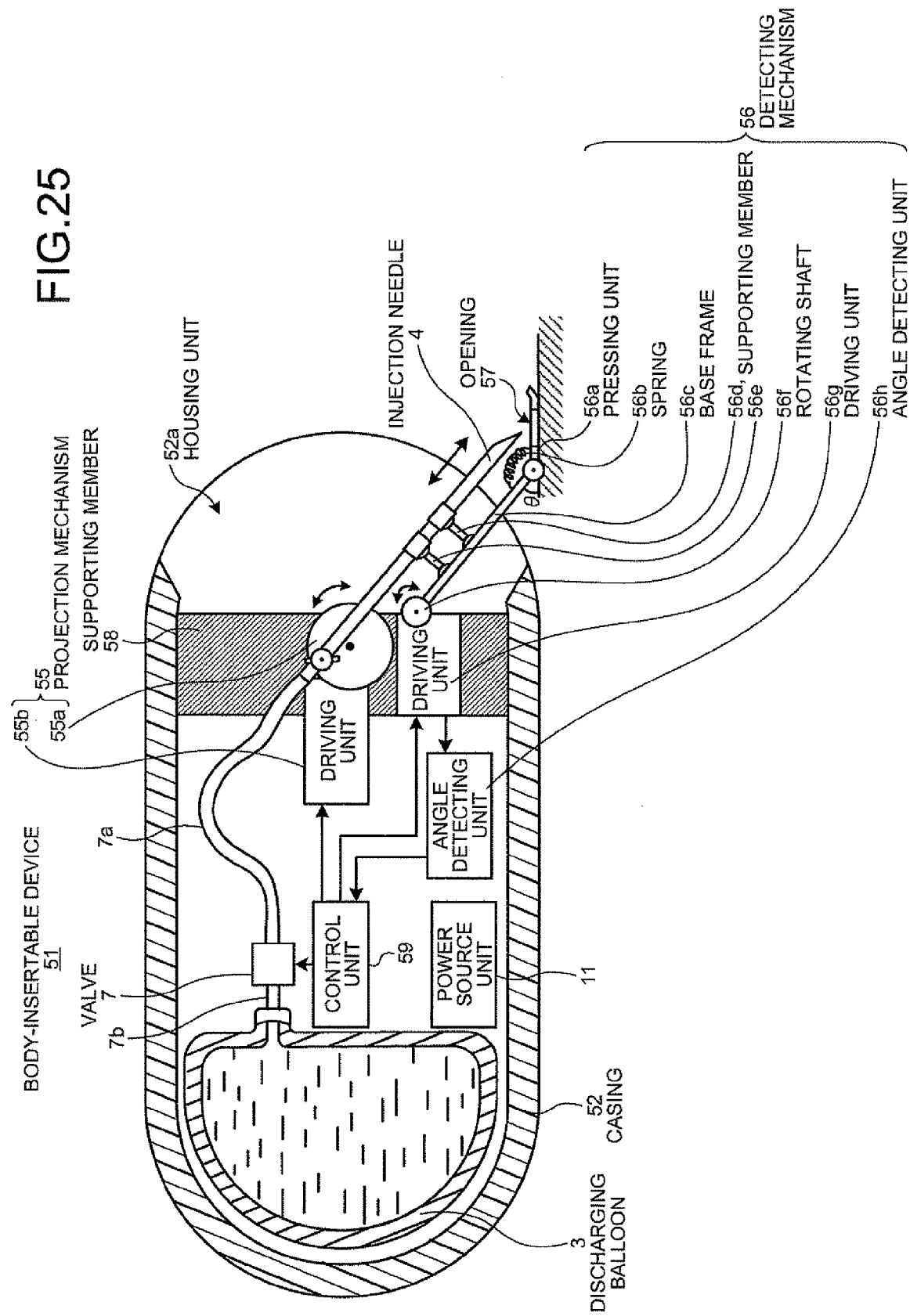
FIG. 25 is a sectional schematic diagram schematically illustrating a configuring example of a body-insertable device according to the fifth embodiment of the present invention.
Figure 26:
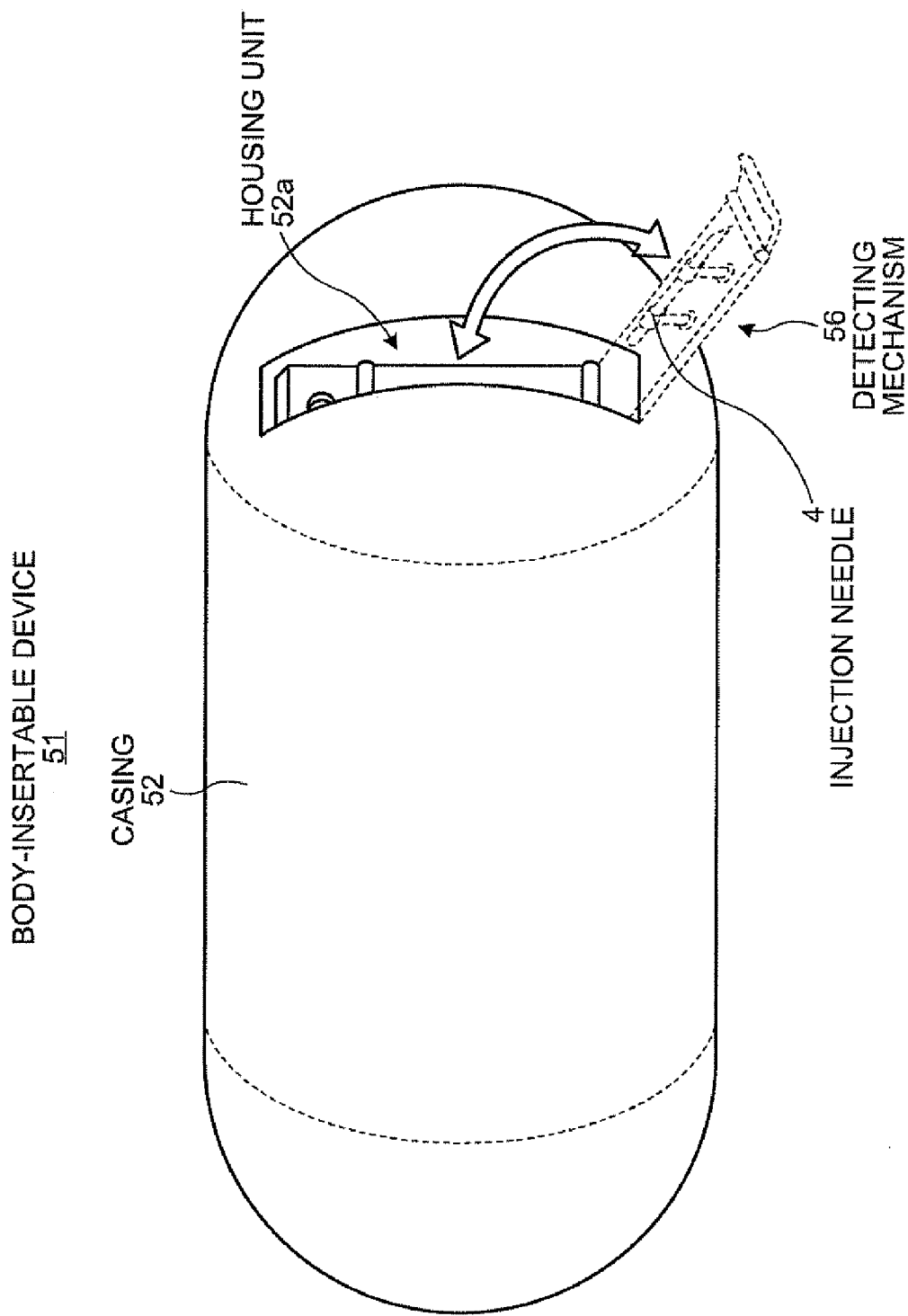
FIG. 26 is a perspective view schematically illustrating the appearance of the body-insertable device according to the fifth embodiment of the present invention, seen from its front end.

FIG. 25 is a sectional schematic diagram schematically illustrating a configuring example of the body-insertable device according to the fifth embodiment of the present invention. FIG. 26 is a perspective view schematically illustrating the appearance of the body-insertable device according to the fifth embodiment of the present invention, seen from its front end. As illustrated in FIG. 25, a body-insertable device 51 has a casing 52 in place of the casing 2 of the body-insertable device 1 according to the first embodiment. The body-insertable device 51 has, in the casing 52, a projection mechanism 55 in place of the projection mechanism 5 of the body-insertable device 1 according to the first embodiment, a control unit 59 in place of the control unit 10, and a detecting mechanism 56. The body-insertable device 51 does not have the guide member 6 and the imaging unit 8 of the body-insertable device 1. The body-insertable device 51 has a supporting member 58 which supports the projection mechanism 55 and the detecting mechanism 56 near a front end of the casing 52. The color markers are not provided on the injection needle 4. Other configuration is the same as that of the first embodiment. The same configuring parts are indicated by similar reference numerals, and the description is omitted.

In substantially the same manner as that of the casing 2 of the body-insertable device 1 according to the first embodiment, the casing 52 is a capsule-type casing formed in a size which can be easily introduced into the body. Specifically, the casing 52 has the front end in a longitudinal direction a housing unit 52a which houses the detecting mechanism 56 together with the injection needle 4. The housing unit 52a is a spatial region formed in recess shape at the front end of the casing 52. As illustrated in FIG. 26, the housing unit 52a houses the detecting mechanism 56 together with the injection needle 4 by rotational driving of the detecting mechanism 56.

The projection mechanism 55 functions as projecting means which projects the injection needle 4 from the casing 52. Specifically, the projection mechanism 55 has a rotating shaft 55a which reciprocates the injection needle 4 which is supported by the detecting mechanism 56 so as to be reciprocated in its longitudinal direction, and a driving unit 55b which rotatably drives the rotating shaft 55a. The driving unit 55b is realized using a motor generating a driving force which rotatably drives the rotating shaft 55a. When the injection needle 4 is projected toward the biological tissue surface, the driving unit 55b rotatably drives the rotating shaft 55a illustrated in FIG. 25 clockwise. When the injection needle 4 is moved in the direction moving away from the biological tissue surface, the driving unit 55b rotatably drives the rotating shaft 55a illustrated in FIG. 25 counterclockwise. Using the driving force of the rotational driving transmitted by the driving unit 55b, the rotating shaft 55a functions to reciprocate the injection needle 4 in its longitudinal direction. The rotating shaft 55a is attached such that the vicinity of the base end of the injection needle 4 is rotatable. The rotating shaft 55a converts the driving force of the rotational driving transmitted by the driving unit 55b to the driving force of the reciprocating operation of the injection needle 4. The rotating shaft 55a is rotatably driven clockwise to project the injection needle 4 toward the biological tissue surface. The rotating shaft 55a is rotatably driven counterclockwise to move the injection needle 4 in the direction moving away from the biological tissue surface.

The detecting mechanism 56 functions as detecting means which supports the injection needle 4 such that it can be reciprocated in its longitudinal direction and detects the position relation between the injection needle 4 and the biological tissue surface in the body. Specifically, the detecting mechanism 56 has a pressing unit 56a which presses the biological tissue surface when detecting the position relation between the injection needle 4 and the biological tissue surface in the body, a spring 56b which generates a pressing force of the pressing unit 56a, and a base frame 56c which is rotatably driven about a rotating shaft 56f to move the pressing unit 56a to the biological tissue surface. The detecting mechanism 56 also has supporting members 56d and 56e which support the injection needle 4 such that the injection needle 4 is parallel with the base frame 56c and reciprocated, a driving unit 56g which generates a driving force which rotatably drives the base frame 56c about the rotating shaft 56f, and an angle detecting unit 56h which detects the puncture angle θ of the injection needle 4 with respect to the biological tissue surface according to the rotation angle of the rotating shaft 56f.

The pressing unit 56a is a plate-like member having an opening 57 which inserts the injection needle 4, and is rotatably connected to one end of the base frame 56c. The pressing unit 56a is moved between the housing unit 52a of the casing 52 and the biological tissue surface in the body together with the base frame 56c rotatably driven about the rotating shaft 56f. Upon movement on the biological tissue surface by rotational driving of the base frame 56c, the pressing unit 55a presses the biological tissue surface using a resilient force of the spring 56b. The pressing unit 56a presses the biological tissue surface, and then makes the uneven biological tissue surface substantially flat. The puncture angle θ of the injection needle 4 which punctures the biological tissue through the opening 57 of the pressing unit 56a becomes substantially equal to the angle formed between the biological tissue surface and the base frame 56c.

The spring 56b generates the pressing force of the pressing unit 56a which presses the biological tissue surface. Specifically, the spring 56b has one end fixed to the pressing unit 56a and the other end fixed to the base frame 56c, and is maintained so as to be shorter than a natural length. The thus-arranged spring 56b can urge the resilient force sufficient to press the pressing unit 56a onto the biological tissue surface, that is, the pressing force to the pressing unit 56a.

The base frame 56c has one end rotatably connected to the pressing unit 56a and the other end connected to the rotating shaft 56f. The base frame 56c is rotatably driven about the rotating shaft 56f to move the pressing unit 56a between the housing unit 52a of the casing 52 and the biological tissue surface in the body. The base frame 56c is connected to the injection needle 4 via the supporting members 56d and 56e so as to reciprocate the injection needle 4. The base frame 56c is rotatably driven clockwise about the rotating shaft 56f. The base frame 56c moves the pressing unit 56a onto the biological tissue surface, and initially arranges the injection needle 4 onto the biological tissue surface in the predetermined position. The tip of the injection needle 4 initially arranged by the base frame 56c is away from the biological tissue surface by a predetermined distance. The base frame 56c is rotatably driven counterclockwise about the rotating shaft 56f. The base frame 56c is housed in the housing unit 52a of the casing 52 together with the injection needle 4 and the pressing unit 56a. The base end of the injection needle 4 is rotatably driven with respect to the rotating shaft 55a.

The supporting members 56d and 56e support the injection needle 4 such that the injection needle 4 is parallel with the base frame 56c and reciprocated. Specifically, the supporting members 56d and 56e each have one end rotatably connected to the base frame 56c and the other end rotatably connected to the injection needle 4. The supporting members 56d and 56e maintain the base frame 56c and the injection needle substantially parallel with each other without obstructing the reciprocating operation of the injection needle 4 by the projection mechanism 55.

The driving unit 56g is realized using a motor generating a driving force which rotatably drives the rotating shaft 56f. The driving unit 56g rotatably drives the rotating shaft 56f to rotatably drive the base frame 56c. Specifically, when the driving unit 56g rotatably drives the base frame 56c from the housing unit 52a toward the biological tissue surface, that is, when the pressing unit 56a is moved onto the biological tissue surface and the injection needle 4 is initially arranged, the rotating shaft 56f illustrated in FIG. 25 is rotatably driven clockwise. When housing the base frame 56c in the housing unit 52a together with the injection needle 4 and the pressing unit 56a, the driving unit 56g rotatably drives the rotating shaft 56f illustrated in FIG. 25 counterclockwise. When rotating and driving the base frame 56c toward the biological tissue surface or the housing unit 52a, the driving unit 56g detects a physical load applied to the rotating shaft 56f. When the physical load is a predetermined value or above, the driving unit 56g stops rotational driving of the rotating shaft 56f. The driving unit 56g can move one end of the base frame 56c and the pressing unit 56a onto the biological tissue surface without excessively pressing the base frame 56c onto the biological tissue surface or the casing 52. Alternatively, the driving unit 56g can house the injection needle 4, the pressing unit 56a, and the base frame 56c in the housing unit 52a.

The angle detecting unit 56h detects the puncture angle θ of the injection needle 4 with respect to the biological tissue surface according to the rotation angle of the rotating shaft 56f. Specifically, the angle detecting unit 56h obtains the rotation angle of the rotating shaft 56f rotatably driven by the driving unit 56g from the driving unit 56g. According to the rotation angle of the rotating shaft 56f, the angle detecting unit 56h detects the angle formed between the biological tissue surface and the base frame 56c, that is, the puncture angle θ of the injection needle 4 with respect to the biological tissue surface. The angle detecting unit 56h brings the state in which the base frame 56c is parallel with the longitudinal direction of the casing 52 into a reference state of the puncture angle θ (that is, a state in which the puncture angle θ is 0°). The angle detecting unit 56h detects, as the puncture angle θ, the rotation angle of the rotating shaft 56f rotatably driven before the reference state is changed to the state in which the pressing unit 56a is moved onto the biological tissue surface. The angle detecting unit 56h notifies the detected puncture angle θ of the injection needle 4 to the control unit 59.

The detecting mechanism 56 having such a configuration presses the pressing unit 56a onto the biological tissue surface in the body to physically detect the position of the biological tissue surface. The detecting mechanism 56 initially arranges the injection needle 4 into the biological tissue surface. The detecting mechanism 56 can detect, as the position relation between the biological tissue surface in the body and the injection needle 4, the amount of projection of the injection needle 4 necessary for reaching the biological tissue surface and the puncture angle θ of the injection needle 4. As illustrated in FIG. 26, the detecting mechanism 56 can house the injection needle 4 in the housing unit 52a of the casing 52.

The supporting member 58 supports the projection mechanism 55 and the detecting mechanism 56. Specifically, the supporting member 58 is fixed to near the front end of the casing 52, supports the driving units 55b and 56g, and rotatably supports the rotating shafts 55a and 56f. The supporting member 58 arranges the injection needle 4, the projection mechanism 55, and the detecting mechanism 56 near the front end of the casing 52. The supporting member 58 secures the water-tight state of the inner space of the casing 52 in which the control unit 59 is arranged.

The control unit 59 controls driving of the projection mechanism 55, the detecting mechanism 56, and the valve 7. Specifically, the control unit 59 controls driving of the driving unit 56g of the detecting mechanism 56 to move the pressing unit 56a onto the biological tissue surface, and initially arranges the injection needle 4. The control unit 59 controls driving of the driving unit 55b of the projection mechanism 55 to reciprocate the injection needle 4 in its longitudinal direction, and then controls the amount of projection of the injection needle 4. The control unit 59 controls the amount of projection of the injection needle 4 corresponding to the puncture angle θ detected by the angle detecting unit 56h. The control unit 59 controls the amount of projection of the injection needle 4 to reliably control the puncture depth of the injection needle 4 from the biological tissue surface to the desired puncture depth. In substantially the same manner as that of the control unit 10 of the body-insertable device 1 according to the first embodiment, the control unit 59 controls driving of the valve 7 to start or stop the discharging operation of the liquid medicine by the discharging balloon 3.

A configuration which defines the timing at which the control unit 59 starts to control driving of the detecting mechanism 56 may have a timer mechanism or may incorporate a radio receiving mechanism to feed a control signal from the outside to the control unit 59. Upon notification of the puncture angle θ from the angle detecting unit 56h, the control unit 59 controls driving of the driving unit 55b to project the injection needle 4. The control unit 59 performs driving control which projects the injection needle 4 by the amount of projection corresponding to the puncture angle θ to the driving unit 55b. The control unit 59 controls open-driving of the valve 7 to start the discharging operation of the liquid medicine by the discharging balloon 3.

Figure 27:
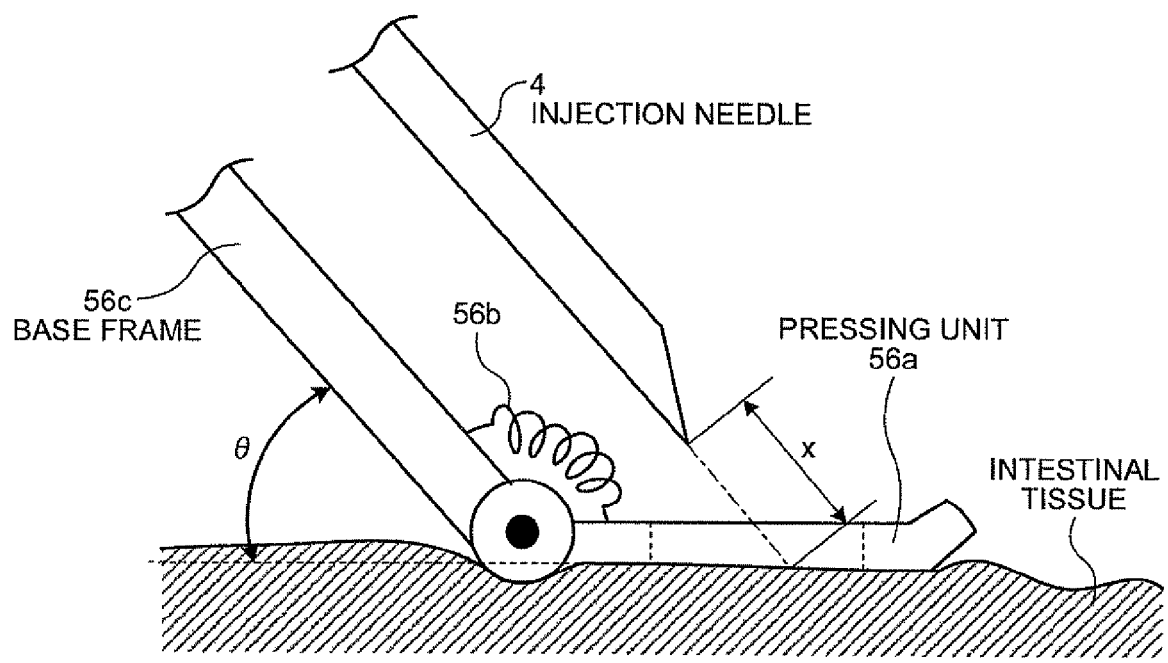
FIG. 27 is a schematic diagram schematically illustrating the state in which the injection needle is initially arranged onto the biological tissue surface in the body.
Figure 28:
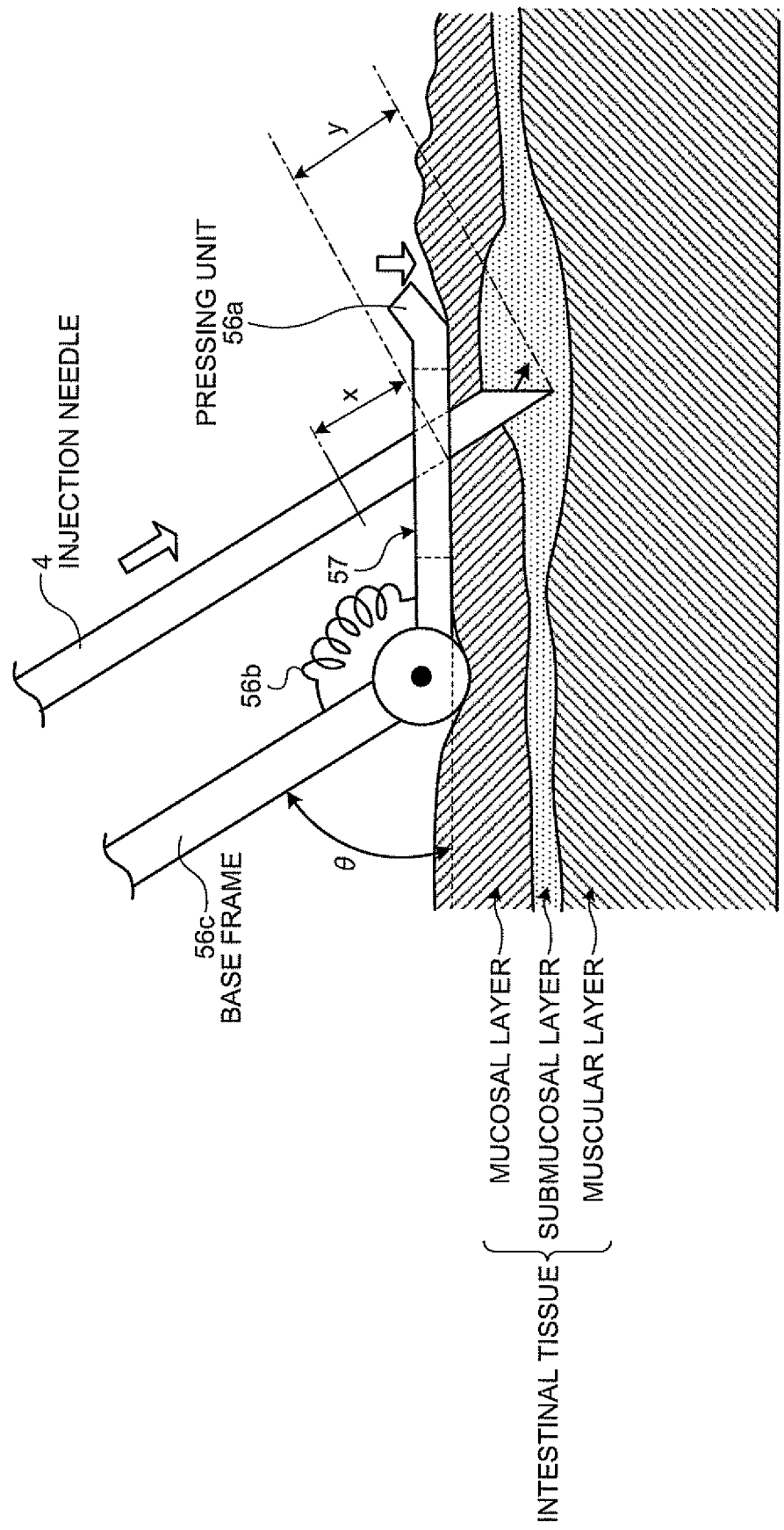
FIG. 28 is a schematic diagram for explaining the operation of a control unit which controls the amount of projection of the injection needle corresponding to the puncture angle.

The operation of the body-insertable device 51 which controls the puncture depth of the injection needle 4 which punctures the desired part in the body to the desired puncture depth will be specifically described. FIG. 27 is a schematic diagram schematically illustrating the state in which the injection needle 4 is initially arranged into the biological tissue surface in the body. FIG. 28 is a schematic diagram for explaining the operation of the control unit 59 which controls the amount of projection of the injection needle 4 corresponding to the puncture angle θ. The operation of the control unit 59 which controls the puncture depth of the injection needle 4 to the desired puncture depth will be described below with reference to FIGS. 27 and 28 by illustrating the case in which the liquid medicine is injected into the submucosal layer of the small intestine which is an example of the desired part in the body.

In step S103 of the processing procedure in steps S101 to S107 (see FIG. 3), in place of performing the image processing to the image which images the injection needle 4 on the projection trajectory, the body-insertable device 51 presses the pressing unit 56a onto the biological tissue surface to physically detect the position relation between the biological tissue surface and the injection needle 4. In step S105, according to the necessary amount of projection and the puncture angle of the injection needle 4 detected as the position relation between the injection needle 4 and the biological tissue surface, the body-insertable device 51 controls the puncture depth of the injection needle 4 from the biological tissue surface to the desired puncture depth. The remaining processing procedure (steps S101, S102, S104, S106, and S107) of the body-insertable device 51 is the same as that of the first embodiment.

The body-insertable device 51 introduced into the body reaches the desired part, e.g., the small intestine, in the body. The control unit 59 controls driving of the driving unit 56g of the detecting mechanism 56 to rotatably drive the rotating shaft 56f, and then rotatably drives the base frame 56c toward the intestinal tissue surface. According to control of the control unit 59, as illustrated in FIG. 27, the base frame 56c moves the pressing unit 56a onto the intestinal tissue surface, and forms the puncture angle θ with respect to the intestinal tissue surface to initially arrange the injection needle 4. The pressing unit 56a presses the intestinal tissue using the resilient force of the spring 56b to make the intestinal tissue surface substantially flat. The initially arranged injection needle 4 forms the puncture angle θ with respect to the intestinal tissue surface. The injection needle 4 is brought into the state in which its tip is away from the intestinal tissue surface by the predetermined distance, that is, the state in which it is arranged in the position of the amount of projection at reach x. As illustrated in FIG. 27, the amount of projection at reach x is the amount of projection of the injection needle 4 necessary for the tip of the initially arranged injection needle 4 to reach the intestinal tissue surface.

The angle detecting unit 56h obtains, from the driving unit 56g, the rotation angle of the rotating shaft 56f which is rotatably driven for initially arranging the injection needle 4. The angle detecting unit 56h detects the puncture angle θ of the injection needle 4 with respect to the intestinal tissue surface according to the rotation angle of the rotating shaft 56f. The angle detecting unit 56h notifies the detected puncture angle θ of the injection needle 4 to the control unit 59.

The control unit 59 controls driving of the driving unit 55b of the projection mechanism 55 according to the puncture angle θ detected by the angle detecting unit 56h. The control unit 59 controls the amount of projection of the injection needle 4 corresponding to the puncture angle θ. The control unit 59 calculates the amount of projection under surface y of the injection needle 4 as illustrated in FIG. 28 according to the puncture angle θ. The control unit 59 adds the amount of projection under surface y and the amount of projection at reach x to determine the total amount of projection of the injection needle 4 corresponding to the puncture angle θ. The amount of projection under surface y is the amount of projection from the biological tissue surface necessary for the injection needle 4 forming the puncture angle θ to puncture the biological tissue to the desired puncture depth.

The control unit 59 controls driving of the driving unit 55b so as to project the injection needle 4 by the calculated total amount of projection. According to control of the control unit 59, the injection needle 4 is projected from the initially arranged state by the total amount of projection. As illustrated in FIG. 28, the injection needle 4 punctures the intestinal tissue to the puncture depth which locates the duct line at the tip into the submucosal layer. The control unit 59 controls the puncture depth of the injection needle 4 to the puncture depth preferable for injecting the liquid medicine into the submucosal layer of the intestinal tissue (that is, the desired puncture depth). The control unit 59 controls driving of the valve 7, and as illustrated in FIG. 28, can inject the predetermined amount of the liquid medicine into the submucosal layer via the injection needle 4.

The body-insertable device 51 completes injection of the liquid medicine into the desired part in the body. The control unit 59 controls driving of the driving unit 55b to pull out the injection needle 4 from the biological tissue, and then returns it into the initially arranged state. The control unit 59 controls driving of the driving unit 56g to rotatably drive the rotating shaft 56f. The control unit 59 houses the injection needle 4, the pressing unit 56a, and the base frame 56c in the housing unit 52a of the casing 52. The body-insertable device 51 can be moved in the digestive tract in the body without puncturing other parts in the body by the injection needle 4 with no intention.

As described above, in the fifth embodiment of the present invention, the body-insertable device 51 has the above configuration. The body-insertable device can have the same operation and effect as those of the first embodiment and easily detect the puncture angle of the injection needle with respect to the biological tissue surface. The body-insertable device which can reliably control the puncture depth of the injection needle which punctures the biological tissue surface to the desired puncture depth can be realized.

When the injection needle punctures the biological tissue, the biological tissue surface is pressed so as to be substantially flat. Sliding of the injection needle on the biological tissue surface can be suppressed. Shifting of the puncture position of the injection needle can be suppressed. The injection needle can easily puncture the desired biological tissue.

Figure 29:
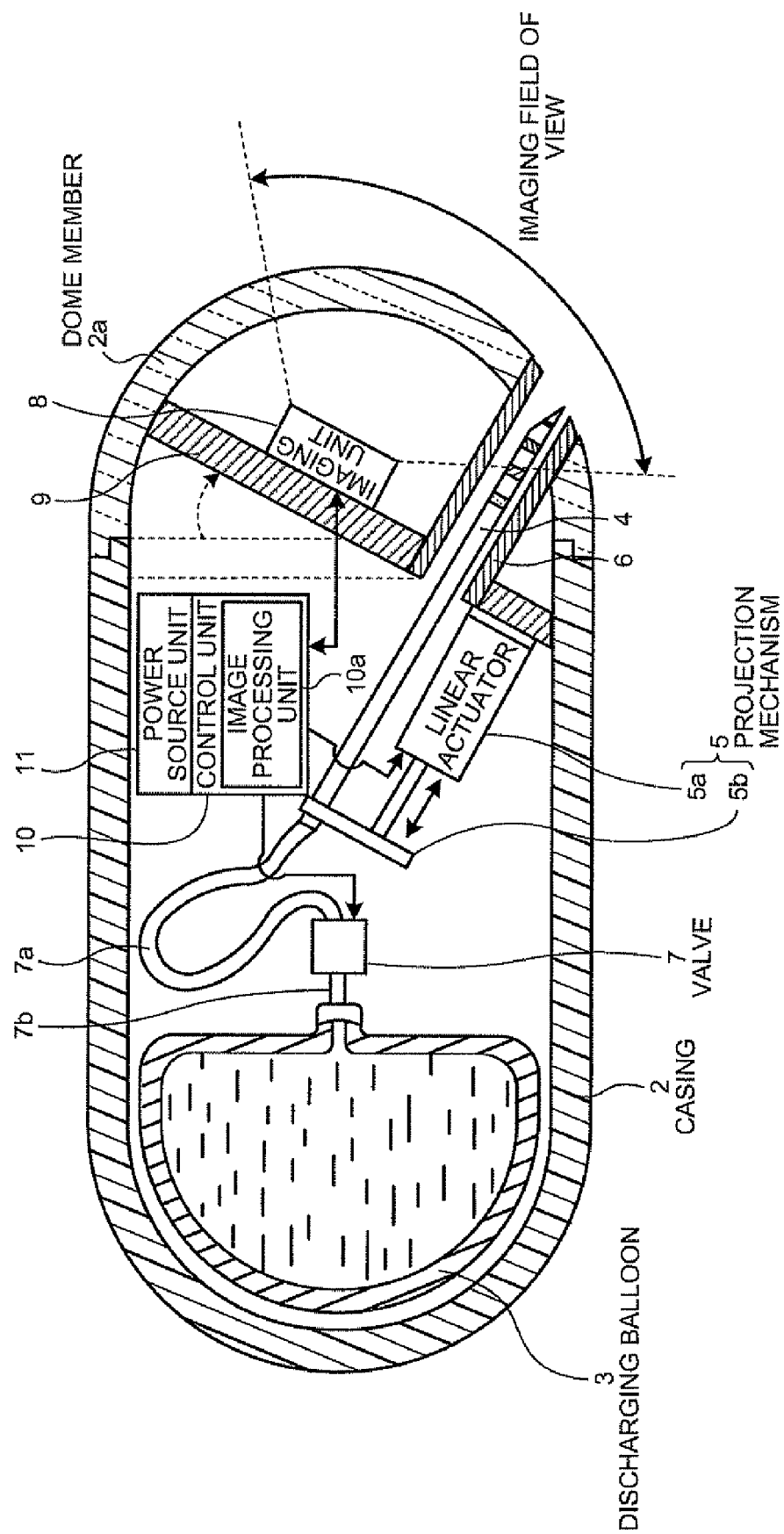
FIG. 29 is a sectional schematic diagram schematically illustrating a configuring example of the body-insertable device according to a modification of the first embodiment of the present invention.
Figure 30:
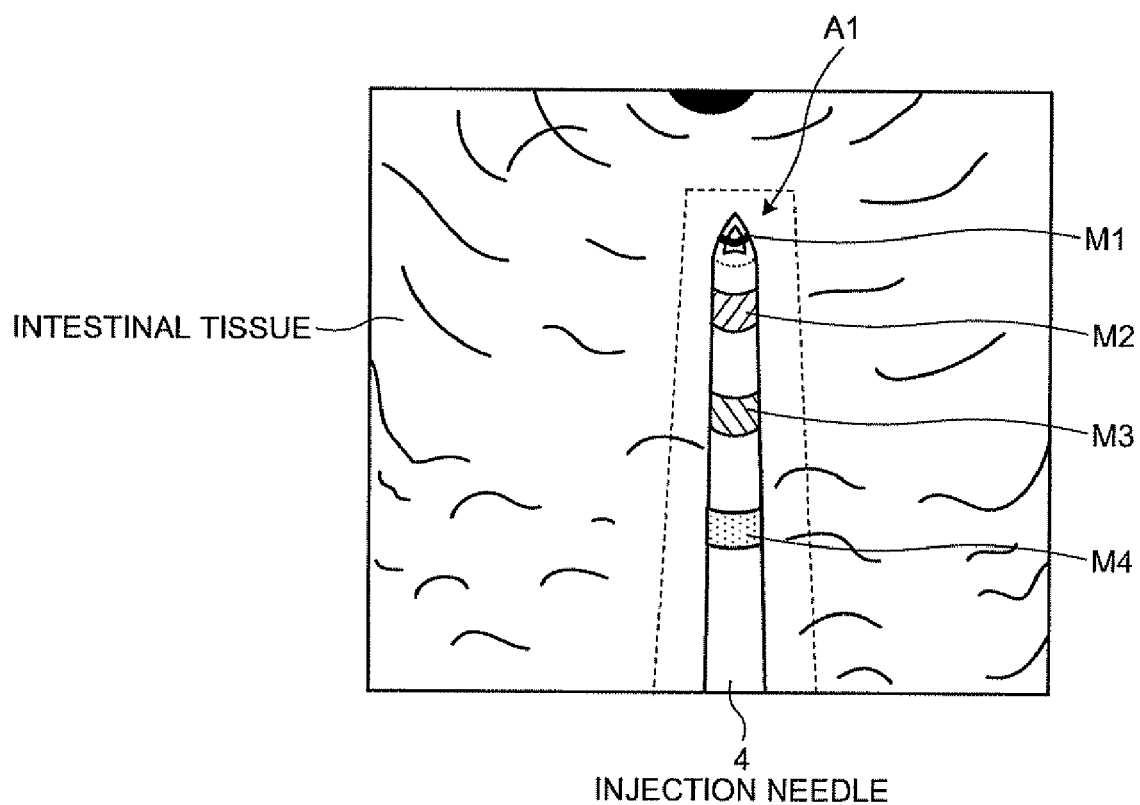
FIG. 30 is a schematic diagram illustrating a specific example of an image imaged by the imaging unit of the body-insertable device according to the modification of the first embodiment.

In the first, the third, and the fourth embodiments of the present invention, the imaging unit 8 is arranged at the front end of the casing 2 such that the angle formed between the light receiving surface of the imaging unit 8 and the longitudinal direction of the casing 2 is a substantially right angle. The present invention is not limited to this. The imaging unit 8 may be tiltably arranged such that the light receiving surface is directed toward the injection needle 4. Specifically, as illustrated in FIG. 29, in the body-insertable device 1 according to the first embodiment, the supporting member 9 should be tiltably arranged toward the front end of the casing 2 such that the angle formed between the light receiving surface of the imaging unit 8 and the longitudinal direction of the injection needle 4 is a substantially right angle. The imaging unit 8 can image the injection needle 4 in the imaging field of view such that the injection needle 4 is in the substantially original shape. As illustrated in FIG. 30, the imaging unit 8 can image the injection needle 4 projected toward the intestinal tissue such that the injection needle 4 has the substantially original length. The color marker provided on the injection needle 4 is easy to be detected. The position relation between the biological tissue surface in the body and the injection needle 4 is easy to be detected. The same applies to the third and the fourth embodiments.

In the first to the third embodiments of the present invention, four or six color markers indicating the puncture depth are provided on the injection needle 4 at predetermined intervals. The present invention is not limited to this. A plurality of color markers indicating the puncture depth may be formed on the injection needle 4. The plurality of color markers may be formed on the injection needle 4 at predetermined intervals, or may be continuously formed without any space.

In the first to the third embodiments of the present invention, a plurality of color markers colored in different colors are provided on the injection needle 4. The present invention is not limited to this. The plurality of color markers colored in a single color which is easy to be distinguished from the biological tissue surface may be provided on the injection needle 4 at predetermined intervals. The control unit 10 detects the amount of projection of the injection needle 4 according to driving of the linear actuator 5a projecting the injection needle 4. The control unit 10 can judge the position relation between the injection needle 4 and the biological tissue surface according to the number of color markers and the amount of projection of the injection needle 4 detected from the detection region of an image by the imaging unit 8. The control unit 10 should control the puncture depth of the injection needle 4 according to the position relation between the injection needle 4 and the biological tissue surface. The same applies to the control units 23 and 33.

In place of providing the plurality of color markers on the injection needle 4, the injection needle 4 itself may be colored in a single color which is easy to be distinguished from the biological tissue surface. The control unit 10 detects the amount of projection of the injection needle 4 according to driving of the linear actuator 5a. The control unit 10 detects the shape of the injection needle 4 according to an image by the imaging unit 8. The control unit 10 can judge the position relation between the injection needle 4 and the biological tissue surface according to the shape and the amount of projection of the injection needle 4 detected from the image. The control unit 10 should control the puncture depth of the injection needle 4 according to the position relation between the injection needle 4 and the biological tissue surface. The same applies to the control units 23 and 33.

In the second and the third embodiments of the present invention, the puncture depth of the injection needle 4 is controlled corresponding to the puncture angle θ of the injection needle 4. The present invention is not limited to this. An angle adjusting mechanism which rotatably drives the projection mechanism 5 together with the injection needle 4 to adjust the puncture angle θ of the injection needle 4 may be provided. The control unit 23 may make the amount of projection of the injection needle 4 from the biological tissue surface substantially constant, and may control the puncture angle θ to control the puncture depth of the injection needle 4 to the desired puncture depth. The same applies to the control unit 33.

In the fourth embodiment of the present invention, when there is no spread of the liquid sump Q of the colored liquid medicine on the biological tissue surface, it is judged that the puncture depth of the injection needle 4 is controlled to the desired puncture depth. The present invention is not limited to this. A washing mechanism which washes away the liquid sump Q on the biological tissue surface may be provided. Each time spread of the colored liquid medicine on the biological tissue surface is detected, the liquid sump of the colored liquid medicine may be washed. When detecting the colored liquid medicine which thinly appears through the biological tissue surface, the control unit 44 judges that the puncture depth of the injection needle 4 is controlled to the desired puncture depth. When not detecting the colored liquid medicine flowed out from the tip of the injection needle 4, the control unit 44 judges that the injection needle 4 excessively punctures the biological tissue surface (the puncture depth is excessive). When judging that the puncture depth of the injection needle 4 is excessive, the control unit 44 returns the injection needle 4 to control the puncture depth to the desired puncture depth.

The washing mechanism may have a discharging balloon which includes a cleaning solution such as a physiological salt solution, and a tube which communicates the discharging balloon with the valve 7. The valve 7 should alternately open- and close-drive discharging openings of the discharging balloon 3 and the discharging balloon of the washing mechanism according to control of the control unit 44.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A body-insertable device, configured to be introduced into a desired part in a body for injecting a liquid medicine stored in a casing into the desired part, the body-insertable device comprising:
    a projecting portion which projects an injection needle injecting the liquid medicine toward the desired part, the injection needle having a plurality of angle detection markers each having a predetermined width in a longitudinal direction of the injection needle;
    an imaging unit which images an image including the injection needle projected from the casing;
    an angle detecting unit which detects the angle detection markers from the image, and calculates a puncture angle, formed between a biological tissue surface in the desired part and the injection needle, based on a result of the detection; and
    a control unit which controls a puncture depth of the injection needle from a biological tissue surface in the desired part based on the calculated puncture angle of the injection needle and the plurality of angle detection markers.

2. The body-insertable device according to claim 1, wherein
    the angle detection markers are color markers each indicating a distance from a tip of the injection needle, and
    the angle detecting unit detects, from the image, the color markers near a puncturing portion of the injection needle which punctures the desired part from the plurality of color markers and calculates the puncture angle of the injection needle based on a figure of the color markers near the puncturing portion.

3. The body-insertable device according to claim 1, further comprising a circular ring marker which is slidably provided at a tip of the injection needle and changes its angle with respect to the injection needle corresponding to the biological tissue surface in the desired part punctured by the injection needle, wherein
    the imaging unit fixes a first angle formed between a light receiving surface thereof and the injection needle and images the image including the injection needle projected from the casing and the ring marker, and
    the angle detecting unit calculates a second angle formed between a plane formed by the ring marker and the light receiving surface according to a shape of the ring marker detected according to the image, and calculates the puncture angle of the injection needle based on the first angle and the second angle.

4. A liquid medicine injection method comprising:

introducing a body-insertable device having a liquid medicine and an injection needle injecting the liquid medicine in a casing into a desired part in a body;

projecting the injection needle from the body-insertable device to the desired part, the injection needle having a plurality of angle detection markers each having a predetermined width in a longitudinal direction of the injection needle;

detecting the angle detection markers and calculating a puncture angle formed between a biological tissue surface in the desired part and the injection needle based on a result of the detection; and controlling a puncture depth of the injection needle from the biological tissue surface based on the calculated puncture angle and the plurality of angle detection markers on the injection needle.

5. The liquid medicine injection method according to claim 4, wherein the detecting includes detecting the angle by imaging an image showing a position relation between the biological tissue surface and the injection needle.

6. The liquid medicine injection method according to claim 5, wherein the controlling includes performing a predetermined image processing on the image showing the position relation and controlling a puncture depth of the injection needle based on the result of the image processing.

* * * * *